United States Patent
Conrad et al.

(10) Patent No.: US 7,878,978 B2
(45) Date of Patent: Feb. 1, 2011

(54) USE OF RELAXIN TO INCREASE ARTERIAL COMPLIANCE

(75) Inventors: Kirk P. Conrad, Cranberry Township, PA (US); Sanjeev G. Shroff, Pittsburgh, PA (US)

(73) Assignee: University of Pittsburgh- Of The Commonwealth System of Higher Education, Pittsburgh, PA (US)

( * ) Notice: Subject to any disclaimer, the term of this patent is extended or adjusted under 35 U.S.C. 154(b) by 1630 days.

(21) Appl. No.: 11/084,670

(22) Filed: Mar. 18, 2005

(65) Prior Publication Data

US 2005/0238639 A1    Oct. 27, 2005

Related U.S. Application Data

(60) Provisional application No. 60/554,716, filed on Mar. 19, 2004.

(51) Int. Cl.
    *A61B 5/00*    (2006.01)
(52) U.S. Cl. .................. 600/485; 600/481; 600/500
(58) Field of Classification Search ................ None
    See application file for complete search history.

(56) References Cited

U.S. PATENT DOCUMENTS

| | | |
|---|---|---|
| 5,166,191 A | 11/1992 | Cronin et al. |
| 5,192,743 A | 3/1993 | Hsu et al. |
| 5,376,638 A | 12/1994 | Young et al. |
| 5,451,572 A | 9/1995 | Cipolla et al. |
| 5,478,807 A | 12/1995 | Cronin et al. |
| 5,612,051 A | 3/1997 | Yue |
| 5,707,642 A | 1/1998 | Yue |
| 5,753,623 A | 5/1998 | Amento et al. |
| 5,759,807 A | 6/1998 | Breece et al. |
| 5,811,395 A | 9/1998 | Schwabe et al. |
| 5,863,552 A | 1/1999 | Yue |
| 5,911,997 A | 6/1999 | Schwabe et al. |
| 5,945,402 A | 8/1999 | Cipolla et al. |
| 5,952,296 A | 9/1999 | Bigazzi |
| 6,048,544 A | 4/2000 | Yue |
| 6,200,953 B1 | 3/2001 | Schwabe et al. |

(Continued)

FOREIGN PATENT DOCUMENTS

EP    0407401 B1    4/1993

(Continued)

OTHER PUBLICATIONS

Conrad et al, "Relaxin Modifies Systemic Arterial Resistance and Compliance in Conscious, Nonpregnant Rats," Endocrinology, vol. 145, No. 7, pp. 3289-3296, 2004.*

(Continued)

*Primary Examiner*—Robert L Nasser
(74) *Attorney, Agent, or Firm*—Lisa M. Matovcik

(57) ABSTRACT

The present invention provides methods for increasing arterial compliance. The methods generally involve administering to an individual in need thereof an effective amount of relaxin. The present invention further provides methods of increasing arterial compliance in individuals who have Type 1 or Type 2 diabetes. The present invention further provides methods of increasing arterial compliance in perimenopausal, menopausal, and post-menopausal women. The present invention further provides methods of increasing arterial compliance in individuals who have or who are at risk of developing age-associated arterial stiffness.

39 Claims, 11 Drawing Sheets

U.S. PATENT DOCUMENTS

| | | |
|---|---|---|
| 6,211,147 B1 | 4/2001 | Unemori |
| 6,251,863 B1 | 6/2001 | Yue |
| 6,267,728 B1 | 7/2001 | Hayden |
| 6,723,702 B2 | 4/2004 | Conrad et al. |
| 6,780,836 B2 | 8/2004 | Unemori |
| 6,949,506 B2 | 9/2005 | Schwabe et al. |
| 6,984,128 B2 | 1/2006 | Breining et al. |
| 6,994,675 B2 * | 2/2006 | Sharrock .................... 600/500 |
| 7,026,360 B1 | 4/2006 | Festo et al. |
| 7,363,076 B2 | 4/2008 | Yun et al. |
| 2002/0019349 A1 | 2/2002 | Conrad et al. |
| 2002/0022593 A1 | 2/2002 | Yue |
| 2004/0185053 A1 | 9/2004 | Govindan |
| 2004/0192606 A1 | 9/2004 | Unemori |
| 2004/0266685 A1 | 12/2004 | Conrad et al. |
| 2005/0026822 A1 | 2/2005 | Tregear et al. |
| 2005/0065159 A1 | 3/2005 | Adams |
| 2005/0119277 A1 | 6/2005 | Gotteland et al. |
| 2005/0143299 A1 | 6/2005 | Bigazzi et al. |
| 2005/0153885 A1 | 7/2005 | Yun et al. |
| 2005/0186526 A1 | 8/2005 | Stewart et al. |
| 2005/0238639 A1 | 10/2005 | Conrad et al. |
| 2005/0240241 A1 | 10/2005 | Yun et al. |
| 2005/0244339 A1 | 11/2005 | Jauernig et al. |
| 2005/0256028 A1 | 11/2005 | Yun et al. |
| 2005/0281781 A1 | 12/2005 | Ostroff |
| 2006/0003928 A1 | 1/2006 | Power et al. |
| 2006/0034847 A1 | 2/2006 | Yun et al. |
| 2006/0083718 A1 | 4/2006 | Ginns et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0247163 A1 | 11/2006 | Unemori |
| 2006/0247172 A1 | 11/2006 | Unemori |
| 2006/0264367 A1 | 11/2006 | Samuel et al. |
| 2006/0269892 A1 | 11/2006 | Breining et al. |
| 2006/0281669 A1 | 12/2006 | Yue |
| 2007/0004619 A1 | 1/2007 | Del Borgo et al. |
| 2007/0086942 A1 | 4/2007 | Chang et al. |
| 2007/0087001 A1 | 4/2007 | Taylor et al. |
| 2007/0104723 A1 | 5/2007 | Power et al. |
| 2007/0105750 A1 | 5/2007 | Dorwald et al. |
| 2007/0140966 A1 | 6/2007 | Chang et al. |
| 2007/0202080 A1 | 8/2007 | Yun et al. |
| 2007/0203058 A1 | 8/2007 | Lau et al. |
| 2007/0260170 A1 | 11/2007 | Levin et al. |
| 2008/0108572 A1 | 5/2008 | Unemori |
| 2008/0166363 A1 | 7/2008 | Govindan et al. |
| 2008/0300172 A1 | 12/2008 | Yue |

FOREIGN PATENT DOCUMENTS

| | | |
|---|---|---|
| EP | 0600010 B1 | 3/2002 |
| EP | 0845992 B1 | 11/2002 |
| EP | 0831871 B1 | 12/2002 |
| EP | 1434599 A1 | 4/2003 |
| EP | 1572242 A1 | 7/2004 |
| EP | 1641824 A1 | 12/2004 |
| EP | 1073470 B1 | 4/2005 |
| EP | 1765149 A2 | 9/2005 |
| EP | 0675732 B1 | 6/2006 |
| EP | 1729817 A1 | 7/2006 |
| EP | 1450792 B1 | 9/2006 |
| EP | 1712220 A1 | 10/2006 |
| EP | 1874358 A2 | 10/2006 |
| EP | 1874824 A2 | 10/2006 |
| EP | 1937724 A2 | 4/2007 |
| EP | 1937851 A2 | 4/2007 |
| EP | 1253929 B1 | 5/2007 |
| EP | 1854476 A2 | 11/2007 |
| EP | 1663294 B1 | 3/2008 |
| WO | WO-89/07945 A1 | 9/1989 |
| WO | WO-93/03755 A2 | 3/1993 |
| WO | WO-94/05317 A1 | 3/1994 |
| WO | WO-95/03822 A2 | 2/1995 |
| WO | WO-95/07098 A1 | 3/1995 |
| WO | WO-95/07711 A1 | 3/1995 |
| WO | WO-96/40185 A1 | 12/1996 |
| WO | WO-96/40186 A1 | 12/1996 |
| WO | WO-97/18774 A1 | 5/1997 |
| WO | WO-97/35600 A1 | 10/1997 |
| WO | WO-00/48618 A1 | 8/2000 |
| WO | WO-00/48636 A1 | 8/2000 |
| WO | WO-01/58468 A1 | 8/2001 |
| WO | WO-02/40500 A2 | 5/2002 |
| WO | WO-03/030930 A1 | 4/2003 |
| WO | WO-03/047570 A1 | 6/2003 |
| WO | WO-2004/011029 A2 | 2/2004 |
| WO | WO-2004/054622 A1 | 7/2004 |
| WO | WO-2004/113381 A1 | 12/2004 |
| WO | WO-2005/023288 A1 | 3/2005 |
| WO | WO-2005/027978 A2 | 3/2005 |
| WO | WO-2005/028516 A2 | 3/2005 |
| WO | WO-2005/037246 A2 | 4/2005 |
| WO | WO-2005/060991 A1 | 7/2005 |
| WO | WO-2005/073164 A1 | 8/2005 |
| WO | WO-2005/089489 A2 | 9/2005 |
| WO | WO-2005/115435 A2 | 12/2005 |
| WO | WO-2006/007372 A2 | 1/2006 |
| WO | WO-2006/054299 A2 | 5/2006 |
| WO | WO-2006/075819 A1 | 7/2006 |
| WO | WO2006/107617 A2 | 10/2006 |
| WO | WO2006/107786 A2 | 10/2006 |
| WO | WO-2006/108556 A2 | 10/2006 |
| WO | WO-2006/138043 A2 | 12/2006 |
| WO | WO-2007/028053 A2 | 3/2007 |
| WO | WO-2007/046103 A2 | 4/2007 |
| WO | WO-2007/046893 A2 | 4/2007 |
| WO | WO-2007/047609 A2 | 4/2007 |
| WO | WO-2007/075270 A2 | 7/2007 |
| WO | WO-2007/075388 A2 | 7/2007 |
| WO | WO-2007/112193 A2 | 10/2007 |
| WO | WO-2009/007848 A2 | 1/2009 |

OTHER PUBLICATIONS

International Search Report and Written Opinion mailed on Oct. 23, 2006 for PCT Application No. PCT/US2005/009149 filed on Mar. 18, 2005, 7 pages.

Novak, J. et al. (Jun. 2001) "Relaxin is Essential for Renal Vasodilation During Pregnancy in Conscious Rats," *The Journal of Clinical Investigation* 107(11):1469-1475.

Supplementary Partial European Search Report mailed Mar. 23, 2009, for EP Application No. 05731443.7 filed Mar. 18, 2005, 4 pages.

Ahokas, R. A. et al. (Sep. 1989). "Lack of Evidence of a Vasodepressor Role for Relaxin in Spontaneously Hypertensive and Normotensive Pregnant Rats," *American Journal of Obstetrics and Gynecology* 161(3):618-622.

Bani, D. et al. (1997). "Relaxin Counteracts Asthma-Like Reaction Induced by Inhaled Antigen in Sensitized Guinea Pigs," *Endocrinology* 138:1909-1915.

Conrad, K. P. et al. (Aug. 2004). "Emerging Role of Relaxin in Renal and Cardiovascular Function," *American Journal of Physiology. Regulatory, Integrative and Comparative Physiology* 287:R250-R261.

Debrah, D. O. et al. (Oct. 2005). "Relaxin Increases Cardiac Output and Reduces Systemic Arterial Load in Hypertensive Rats," *Hypertension* 46:745-750.

Dschietzig, T. et al. (2001). "Flow-Induced Pressure Differentially Regulates Endothelin-1, Urotensin II, Adrenomedullin, and Relaxin in Pulmonary Vascular Endothelium," *Biochemical and Biophysical Research Communications* 289(1):245-251.

Dschietzig, T. et al. (2005). "Myocardial Relaxin Counteracts Hypertrophy in Hypertensive Rats," *Annals of the New York Academy of Sciences* 1041:441-443.

Dschietzig, T. et al. (2007). "A Pilot Safety and Dose-Finding Trial of Intravenous Recombinant Human Relaxin (rhRlx) in Compensated Congestive Heart Failure," *European Heart Journal* 28(Abstract supplement):387, located at <http://spo.escardio.org/abstract-book/presentation.aspx?id=51834> visited on Oct. 9, 2007. (1 page).

Dschietzig, T. et al. (Jan. 2003). "Relaxin, a Pregnancy Hormone, is a Functional Endothelin-1 Antagonist: Attenuation of Endothelin-1-Mediated Vasoconstriction by Stimulation of Endothelin Type-B Receptor Expression Via ERK-1/2 and Nuclear Factor-κB," *Circulation Research* 92:32-40.

Dschietzig, T. et al. (Oct. 2001). "The Pregnancy Hormone Relaxin is a Player in Human Heart Failure," *The FASEB Journal* 15:2187-2195.

Failli, P. et al. (2005). "Effects of Relaxin on Vascular Smooth Muscle and Endothelial Cells in Normotensive and Hypertensive Rats," *Annals of the New York Academy of Sciences* 1041:311-313.

Fisher, C. et al. (2003). "N-Terminal Pro B Type Natriuretic Peptide, but Not the New Putative Cardiac Hormone Relaxin, Predicts Prognosis in Patients with Chronic Heart Failure," *Heart* 89:879-881.

Kristiansson, P. et al. (2001). "Reproductive Hormones and Blood Pressure During Pregnancy," *Human Reproduction* 16:13-17.

Kruger, S. et al. (2004). "Relaxin Kinetics During Dynamic Exercise in Patients with Chronic Heart Failure." *European Journal of Internal Medicine* 15:54-56.

Kupari, M. et al. (2005). "Is the Pregnancy Hormone Relaxin an Important Player in Human Heart Failure?," *The European Journal of Heart Failure* 7:195-198.

Lekgabe, E. D. et al. (2005). "Relaxin Reverses Cardiac and Renal Fibrosis in Spontaneously Hypertensive Rats," *Hypertension* 46:412-418.

Lindheimer, M. D. et al. (Mar. 2001). "The Kidney and Hypertension in Pregnancy: Twenty Exciting Years," *Seminars in Nephrology* 21(2):173-189.

Massicotte, G. et al. (1989). "Blunted Responses to Vasoconstrictors in Mesenteric Vasculature but not in Portal Vein of Spontaneously Hypertensive Rats Treated with Relaxin," *Proceedings of the Society for Experimental Biology and Medicine* 190:254-259.

Parry, L. J. et al. (1990). "Mechanism of the Haemotensive Action of Porcine Relaxin in Anaesthetized Rats," *Journal of Neuroendocrinology* 2(1):53-58.

Samuel, C. S. et al. (2003). "Physiological or Pathological—A Role for Relaxin in the Cardiovascular System?," *Current Opinion in Pharmacology* 3:152-158.

Sherwood, O. D. (2004). "Relaxin's Physiological Roles and Other Diverse Actions," *Endocrine Reviews* 25:205-234.

St-Louis, J. et al. (1985). "Chronic Decrease of Blood Pressure by Rat Relaxin in Spontaneously Hypertensive Rats," *Life Sciences* 37(14):1351-1357.

Teichman, S. L. et al. (2008). "Relaxin, a Pleiotropic Vasodilator for the Treatment of Heart Failure," *Heart Failure Reviews*, epub ahead of print, 9 pages.

Tozzi, C. A. et al. (2005). "Recombinant Human Relaxin Reduces Hypoxic Pulmonary Hypertension in the Rat," *Pulmonary Pharmacology & Therapeutics* 18:346-353.

U.S. Appl. No. 11/191,824, filed Jul. 27, 2005 for Stewart.

U.S. Appl. No. 12/340,636, filed Dec. 19, 2008 for Breining et al.

Ward, D. G. et al. (Jul. 31, 1992). "Relaxin Increases Rat Heart Rate by a Direct Action on the Cardiac Atrium," *Biochemical and Biophysical Research Communications* 186(2):999-1005.

Yang, R. H. et al. (Apr. 1995). "Pressor and Bradycardic Effects of Centrally Administered Relaxin in Conscious Rats," *American Journal of Hypertension* 8(4):375-381.

Debrah, Conrad, Danielson and Shroff; Effects of relaxin on systemic arterial hemodynamics and mechanical properties in conscious rats: sex dependency and dose response.

Chemla et al. (1998) "Total arterial compliance estimated by stroke volume-to-aortic pulse pressure ration in humans," *Am J Physiol Heart Circ Physiol*, 274: 500-505.

Cholley et al. (1995) "Differential effects of chronic oral antihypertensive therapies on systemic arterial circulation and ventricular energetics in African-American patients," *Circulation*, 91: 1052-1062.

Cholley et al. (2001) "Smooth muscle relaxation and local hydraulic impedance properties of the aorta," *J Appl Physiol*, 90: 2427-2438.

Debrah et al. (2006) "Relaxin is essential for systemic vasodilation and increased global arterial compliance during early pregnancy in conscious rats," *Endocrinology*, 147: 5126-5131.

Guerin et al. (2001) "Impact of aortic stiffness attenuation on survival of patients in end-stage renal failure," *Circulation*, 103:987-992.

Hibbard et al. (2005) "The arterial system in pre-eclampsia and chronic hypertension with superimposed pre-eclampsia," *BJOG: International Journal of Obstetrics and Gynaecology*, 112: 1-7.

Mills et al. (2000) "A new method for measurement of blood pressure, heart rate, and activity in the mouse by radiotelemetry," *J Appl Physiol*, 88: 1537-1544.

Van Bortel et al. (1995) "Effects of antihypertensive agents on local arterial distensibility and compliance," *Hypertension*, 26: 531-534.

Office Action received for AU Patent Application No. 2005223694, mailed on Jan. 21, 2010, 2 pages.

Examination Report received for EP Patent Application No. 05731443.7, dated Jun. 24, 2009, 3 pages.

Office Action received for CA Patent Application No. 2559745, dated on Sep. 17, 2009, 2 pages.

Debrah, Conrad, Danielson and Shroff; Effects of relaxin on systemic arterial hemodynamics and mechanical properties in conscious rats: sex dependency and dose response, 2005.

* cited by examiner

USE OF RELAXIN TO INCREASE ARTERIAL COMPLIANCE

CROSS-REFERENCE TO RELATED APPLICATIONS

The present application claims priority to U.S. Patent Application No. 60/554,716, filed Mar. 19, 2004, the teachings of which are hereby incorporated by reference in their entirety.

STATEMENT REGARDING FEDERALLY SPONSORED RESEARCH

The U.S. government may have certain rights in this invention, pursuant to Grant No. RO 1 HL67937 awarded by the National Institutes of Health.

FIELD OF THE INVENTION

The present invention is in the field of arterial compliance, and in particular, the use of relaxin to increase arterial compliance.

BACKGROUND OF THE INVENTION

Arterial compliance declines with age even in healthy individuals with no overt cardiovascular disease. With age, a decrease is seen in the ability of the large and small arteries to distend in response to an increase in pressure. The age-associated reduction in arterial compliance is an independent risk factor for the development of cardiovascular disease, and is associated with a number of other pathological conditions. For example, reduced arterial compliance is also associated with both Type 1 diabetes mellitus and Type 2 diabetes mellitus. It has been reported that diabetic arteries appear to age at an accelerated rate compared to arteries of non-diabetic individuals. See, e.g., Arnett et al. (1994) *Am J Epidemiol.* 140:669-682; Rowe (1987) *Am J Cardiol.* 60:68G-71G; Cameron et al. (2003) *Diabetes Car.* 26(7):2133-8; Kass et al. (2001) *Circulation* 104:1464-1470; Avolio et al. (1983) *Circulation* 68:50-58; U.S. Pat. No. 6,251,863; U.S. Pat. No. 6,211,147.

There is a need in the art for methods of increasing arterial compliance, and for treating disorders associated with or resulting from reduced arterial compliance. The present invention addresses these needs.

SUMMARY OF THE INVENTION

The present invention provides methods of treating individuals with diminished arterial compliance an effective amount of a formulation comprising a relaxin receptor agonist. In a preferred embodiment the relaxin receptor agonist is a recombinant human relaxin, e.g., human H2 relaxin.

In one embodiment of the invention, the invention provides a method of increasing arterial compliance in a subject, wherein said method comprises measuring global arterial compliance in said subject; determining that said global arterial compliance is diminished in said subject relative to global arterial compliance in a healthy subject; and administering to said subject a pharmaceutical formulation comprising relaxin to increase arterial compliance in said subject. Global arterial compliance may be measured, in one embodiment, from the diastolic decay of the aortic pressure waveform using the area method. In another embodiment, global arterial compliance may be calculated as the stroke volume-to-pulse pressure ratio, where the stroke volume is defined as the ratio of cardiac output to heart rate.

In related embodiments, the local arterial compliance or the regional arterial compliance of a subject may be measured in addition to or as an alternative to the global arterial compliance measurement and, if the local or regional arterial compliance is diminished relative to the local or regional arterial compliance expected for a similarly situated healthy individual, relaxin may be administered to increase arterial compliance in that individual.

In further embodiments, the subject to whom relaxin is administered suffers from one or more of the following disorders: atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia. In related embodiments, the invention provides methods of increasing arterial compliance in perimenopausal, menopausal, and post-menopausal women and in individuals who are at risk of one of the aforementioned disorders.

In an additional embodiment of the invention, administration of relaxin increases arterial compliance by at least 10%, 15%, 20% or more, relative to the measured arterial compliance before administration. In still further embodiments, the invention provide for the administration of relaxin to individuals with diminished arterial compliance at a predetermined rate so as to maintain a serum concentration of relaxin from 0.5 to 80 ng/ml. In one embodiment, the relaxin is recombinant human relaxin. In yet another embodiment, the relaxin is recombinant H2 relaxin. In related embodiments, the relaxin may be administered daily, in an injectable formulation, as a sustained release formulation, or as a contiuous infusion.

DEFINITIONS

Figure 1:
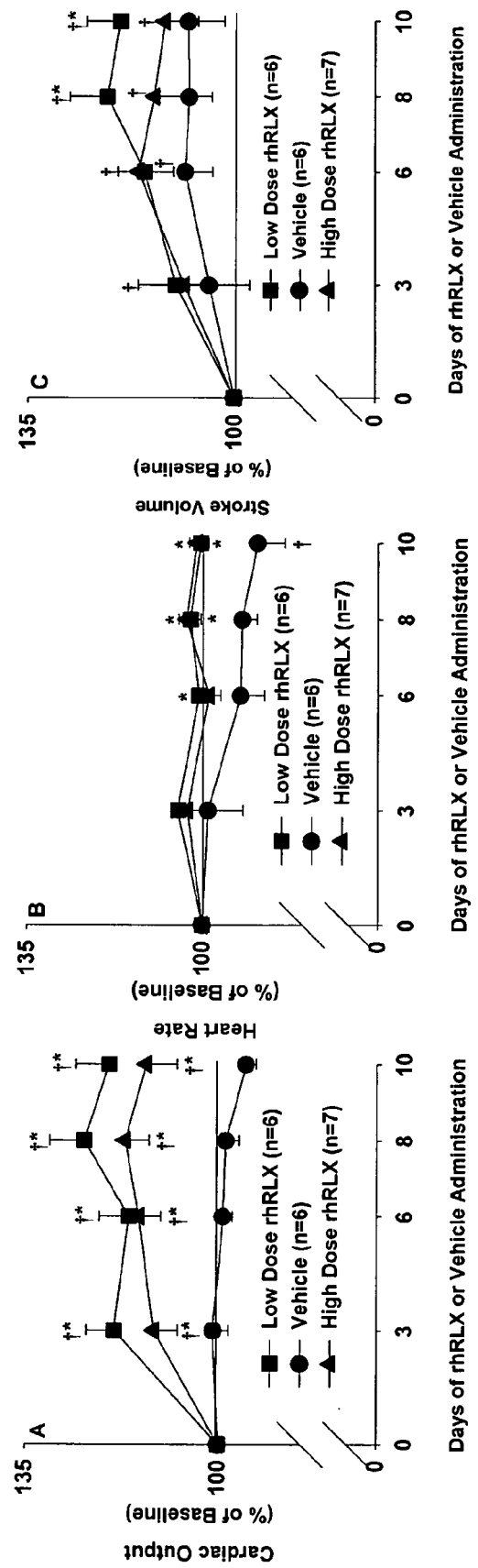
FIGS. 1A-C depict the percent change from baseline for cardiac output (FIG. 1A), heart rate (FIG. 1B), and stroke volume (FIG. 1C) in female rats administered low dose recombinant human relaxin (rhRLX; 4 µg/h), high dose rhRLX (25 µg/h), or vehicle.

The terms "subject," "host," "individual," and "patient," used interchangeably herein, refer to any subject, particularly a mammalian subject, for whom diagnosis or therapy is desired, particularly humans. Other subjects may include cattle, dogs, cats, guinea pigs, rabbits, rats, mice, horses, and so on. In many embodiments, a subject is a human in need of treatment for a disease or condition related to or resulting from reduced arterial compliance.

The terms "treatment," "treating," "therapy," and the like are used herein to generally refer to obtaining a desired therapeutic, pharmacologic or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, e.g. a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used herein the terms "isolated" and "substantially purified," used interchangeably herein, when used in the context of "isolated relaxin," refer to a relaxin polypeptide that is in an environment different from that in which the relaxin polypeptide naturally occurs. As used herein, the term "substantially purified" refers to a relaxin polypeptide that is removed from its natural environment and is at least 60% free, preferably 75% free, and most preferably 90% free from other components with which it is naturally associated.

Before the present invention is further described, it is to be understood that this invention is not limited to the particular embodiments described. The scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a relaxin formulation" includes a plurality of such formulations and reference to "the active agent" includes reference to one or more active agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of treating disorders associated with arterial stiffness; methods of increasing arterial compliance; methods of reducing arterial stiffness in an individual; and methods of reducing the risk that an individual will develop one or more complications or disorders associated with reduced arterial compliance. The methods generally involve administering to an individual in need thereof an effective amount of a relaxin receptor agonist. In some embodiments, the individual has, or is at risk of developing, age-related arterial stiffness. In other embodiments, the individual has Type 1 or Type 2 diabetes, and thus has developed, or is at risk of developing, arterial stiffness. In other embodiments, the individual is a perimenopausal woman, a menopausal woman, or a post-menopausal woman, and thus has developed, or is at risk of developing, arterial stiffness. In still other embodiments, the individual is a women who has or is at risk of developing preeclampsia.

One of the major cardiovascular adaptations in human pregnancy is the increase in global arterial compliance, accompanied by increases in relaxin levels, which reaches a peak by the end of the first trimester just as systemic vascular resistance (SVR) reaches a nadir. At least in theory, the rise in global arterial compliance is critical to the maintenance of cardiovascular homeostasis during pregnancy for several reasons: (1) the rise in global AC prevents excessive decline in diastolic pressure which otherwise would fall to precariously low levels due to the significant decline in SVR; (2) the rise minimizes the pulsatile or oscillatory work wasted by the heart which otherwise would increase in disproportion to the rise in total work required of and expended by the heart during pregnancy; and (3) the rise in global AC preserves steady shear-type (or prevents oscillatory shear-type) stress at the blood-endothelial interface despite the hyperdynamic circulation of pregnancy, thereby favoring production of nitric oxide rather than superoxide and other damaging reactive oxygen species by the endothelium. The increase in global AC, along with the reduction in SVR, can result in circulatory underfilling, and thus, contribute to renal sodium and water retention and plasma volume expansion during early pregnancy.

Treatment Methods

The present invention provides methods for increasing arterial compliance which utilize the step of administering to an individual in need thereof an effective amount of a relaxin receptor agonist. In some embodiments, the individual has atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia, or is at risk of developing age-related arterial stiffness. In other embodiments, the individual is a perimenopausal woman, a menopausal woman, or a post-menopausal woman, or a woman who has ceased menstruation for non-age-related reasons, e.g., due to excessive exercise or as a result of surgery (e.g., hysterectomy, oophorectomy), and has developed, or is at risk of developing, arterial stiffness.

The methods generally involve administering to an individual an effective amount of relaxin. In some embodiments, an effective amount of relaxin is an amount that is effective to increase arterial compliance by at least about 5%, at least about 10%, at least about 15%, at least about 20%, at least about 25%, at least about 30%, at least about 35%, at least about 40%, at least about 45%, or at least about 50%, or more, compared to the arterial compliance in the absence of treatment with relaxin.

In some embodiments, an effective amount of relaxin is an amount that is effective to reduce arterial stiffness by at least about 5%, at least about 10%, at least about 15%, at least about 20%, at least about 25%, at least about 30%, at least about 35%, at least about 40%, at least about 45%, or at least about 50%, or more, compared to the arterial stiffness in the individual in the absence of treatment with relaxin.

In some embodiments, an effective amount of relaxin is an amount that is effective to increase arterial elasticity by at least about 5%, at least about 10%, at least about 15%, at least about 20%, at least about 25%, at least about 30%, at least about 35%, at least about 40%, at least about 45%, or at least about 50%, or more, compared to the arterial elasticity in the individual in the absence of treatment with relaxin.

Disorders resulting from or associated with arterial stiffness or reduced arterial compliance include, but are not limited to, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia. Of particular interest in some embodiments, is arterial stiffness associated with Type 1 diabetes, Type 2 diabetes, normal aging, stroke, diastolic dysfunction, menopause, obesity, hypercholesterolemia, familial hypercholesterolemia, isolated systolic hypertension, long-term tobacco smoking, and left ventricular hypertrophy.

An increase in arterial compliance, or a reduction in arterial stiffness, reduces the risk that an individual will develop a pathological condition resulting from reduced arterial compliance.

In some embodiments, an effective amount of relaxin is an amount that is effective to reduce the risk that an individual will develop a pathological condition associated with or resulting from reduced arterial compliance by at least about 5%, at least about 10%, at least about 15%, at least about 20%, at least about 25%, at least about 30%, at least about 35%, at least about 40%, at least about 45%, or at least about 50%, or more, compared to the risk of developing the condition in the absence of treatment with relaxin.

In general, as discussed above, an effective amount of relaxin is one that is effective to increase arterial compliance. The term "increase" is used interchangeably herein with "stimulate" and "promote." The Examples provide general guidance for effective amounts used in rats. Those skilled in the art will readily be able to determine effective amounts for use in human subjects, given the guidance in the Examples. In general, a dose of relaxin is from about 0.1 to 500 µg/kg of body weight per day, about 6.0 to 200 µg/kg of body weight per day, or about 1.0 to 100 µg/kg of body weight per day. For administration to a 70 kg person, the dosage range would be about 7.0 µg to 3.5 mg per day, about 42.0 µg to 2.1 mg per day, or about 84.0 to 700 µg per day. In some embodiments, for administration to a human, an effective dose is from about 5 µg/kg body weight/day to about 50 µg/kg body weight/day, or from about 10 µg/kg body weight/day to about 25 µg/kg body weight/day. The amount of relaxin administered will, of course, be dependent on the size, sex and weight of the subject and the severity of the disease or condition, the manner and schedule of administration, the likelihood of recurrence of the disease, and the judgment of the prescribing physician. In each case the daily dose may be administered over a period of time, rather than as a single bolus, depending on the effect desired and differences in individual circumstances.

In some embodiments, relaxin is administered to the individual at a predetermined rate so as to maintain a serum concentration of relaxin of from about 0.01 ng/ml to about 80 ng/ml, e.g., from about 0.01 ng/ml to about 0.05 ng/ml, from about 0.05 ng/ml to about 0.1 ng/ml, from about 0.1 ng/ml to about 0.25 ng/ml, from about 0.25 ng/ml to about 0.5 ng/ml, from about 0.5 ng/ml to about 1.0 ng/ml, from about 1.0 ng/ml to about 5 ng/ml, from about 5 ng/ml to about 10 ng/ml, from about 10 ng/ml to about 15 ng/ml, from about 15 ng/ml to about 20 ng/ml, from about 20 ng/ml to about 25 ng/ml, from about 25 ng/ml to about 30 ng/ml, from about 30 ng/ml to about 35 ng/ml, from about 35 ng/ml to about 40 ng/ml, from about 40 ng/ml to about 45 ng/ml, from about 45 ng/ml to about 50 ng/ml, from about 50 ng/ml to about 60 ng/ml, from about 60 ng/ml to about 70 ng/ml, or from about 70 ng/ml to about 80 ng/ml.

Determining Effectiveness

Whether a given relaxin formulation, or a given dosage of relaxin is effective in increasing arterial compliance, reducing arterial stiffness, or increasing arterial elasticity, can be determined using any known method. Arterial stiffness may be measured by several methods known to those of skill in the art, including the methods discussed in the Examples.

One measure of global arterial compliance is the $AC_{area}$ value, which is calculated from the diastolic decay of the aortic pressure waveform [P(t)] using the area method (Liu et al. (1986) *Am. J. Physiol.* 251:H588-H600), as described in the Example, infra. Another measure of global arterial compliance is calculated as the stroke volume to pulse pressure ratio (Chemla et al. (1998) *Am. J. Physiol.* 274:H500-H505), as described in the Example, infra.

Local arterial compliance may be determined by measuring the elasticity of an arterial wall at particular point using invasive or non-invasive means. See, e.g., U.S. Pat. No. 6,267,728. Regional compliance, which describes compliance in an arterial segment, can be calculated from arterial volume and distensibility, and is mainly measured with the use of pulse wave velocity. See, e.g., Ogawa et al., *Cardiovascular Diabetology* (2003) 2:10; Safar et al., *Arch Mal Coer* (2002) 95:1215-18. Other suitable methods of measuring arterial compliance are described in the literature, and any known method can be used. See, e.g., Cohn, J. N., "Evaluation of Arterial Compliance", In: Hypertension Primer, Izzo, J. L. and Black, H. R., (eds.), Pub. by Council on High Blood Pressure Research, American Heart Association, pp. 252-253, (1993); Finkelstein, S. M., et al., "First and Third-Order Models for Determining Arterial Compliance", Journal of Hypertension, 10 (Suppl. 6,) S11-S14, (1992); Haidet, G. C., et al., "Effects of Aging on Arterial Compliance in the Beagle", Clinical Research, 40, 266A, (1992); McVeigh, G. E., et al., "Assessment of Arterial Compliance in Hypertension", Current Opinion in Nephrology and Hypertension, 2, 82-86, (1993).

Relaxin Receptor Agonists

The instant methods involve administration of formulations comprising a pharmaceutically active relaxin receptor agonist. As used herein, the terms "relaxin receptor agonist" and "relaxin" are used interchangeably to refer to biologically active (also referred to herein as "pharmaceutically active") relaxin polypeptides from recombinant or native (e.g., naturally occurring) sources; relaxin polypeptide variants, such as amino acid sequence variants; synthetic relaxin polypeptides; and non-peptide relaxin receptor agonists, e.g., a relaxin mimetic.

Naturally occurring biologically active relaxin may be derived from human, murine (i.e., rat or mouse), porcine, or other mammalian sources. The term "relaxin" encompasses human H1 preprorelaxin, prorelaxin, and relaxin; H2 preprorelaxin, prorelaxin, and relaxin; recombinant human relaxin (rhRLX); and H3 preprorelaxin, prorelaxin, and relaxin. H3 relaxin has been described in the art. See, e.g., Sudo et al. (2003) *J Biol Chem.* 7;278(10):7855-62. The amino acid sequences of human relaxin are described in the art. For example, human relaxin amino acid sequences are found under the following GenBank Accession Nos.: Q3WXF3, human H3 prorelaxin; P04808, human H1 prorelaxin; NP_604390 and NP_005050, human H2 prorelaxin; AAH05956, human relaxin 1 preproprotein; NP_008842, human H1 preprorelaxin; etc. The term "relaxin receptor agonist" includes a human relaxin derived from any one of the aforementioned sequences.

The term "relaxin receptor agonist" also encompasses a relaxin polypeptide comprising A and B chains having N- and/or C-terminal truncations. For example, in H2 relaxin, the A chain can be varied from A(1-24) to A(10-24) and B chain from B(-1-33) to B(10-22); and in H1 relaxin, the A chain can be varied from A(1-24) to A(10-24) and B chain from B(1-32) to B(10-22).

Also included within the scope of the term "relaxin receptor agonist" are relaxin polypeptides comprising insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395, and U.S. Pat. No. 6,200,953. Other suitable relaxins and relaxin formulations are found in U.S. Pat. No. 5,945,402. Also encompassed is a relaxin polypeptide modified to increase in vivo half life, e.g., PEGylated relaxin (i.e., relaxin conjugated to a polyethylene glycol), and the like.

Possible modifications to relaxin polypeptide amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807.

Also encompassed by the term "relaxin receptor agonist" are fusion polypeptides comprising a relaxin polypeptide and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors.

All such variations or alterations in the structure of the relaxin molecule resulting in variants are included within the scope of this invention so long as the functional (biological) activity of the relaxin is maintained. In general, any modification of relaxin amino acid sequence or structure is one that does not increase its immunogenicity in the individual being treated with the relaxin variant. Those variants of relaxin having the described functional activity can be readily identified using the methods discussed herein.

Relaxin Formulations

Relaxin formulations suitable for use in the methods of the invention are pharmaceutical formulations comprising a therapeutically effective amount of pharmaceutically active relaxin, and a pharmaceutically acceptable excipient. The formulation is in some embodiments injectable and in some embodiments designed for intravenous injection.

Any known relaxin formulation can be used in the methods of the present invention, provided that the relaxin is pharmaceutically active. "Pharmaceutically active" relaxin is a form of relaxin which results in increased arterial compliance when administered to an individual.

Relaxin may be administered as a polypeptide, or as a polynucleotide comprising a sequence which encodes relaxin. Relaxin suitable for use in the methods of the present invention can be isolated from natural sources, may be chemically or enzymatically synthesized, or produced using standard recombinant techniques known in the art. Examples of methods of making recombinant relaxin are found in various publications, including, e.g., U.S. Pat. Nos. 4,835,251; 5,326,694; 5,320,953; 5,464,756; and 5,759,807.

Relaxin suitable for use includes, but is not limited to, human relaxin, recombinant human relaxin, relaxin derived from non-human mammals, such as porcine relaxin, and any of a variety of variants of relaxin known in the art. Relaxin, pharmaceutically active relaxin variants, and pharmaceutical formulations comprising relaxin are well known in the art. See, e.g., U.S. Pat. Nos. 5,451,572; 5,811,395; 5,945,402; 5,166,191; and 5,759,807, the contents of which are incorporated by reference in their entirety for their teachings relating to relaxin formulations, and for teachings relating to production of relaxin. In the Examples described herein, recombinant human relaxin (rhRLX) is identical in amino acid sequence to the naturally occurring product of the human H2 gene, consisting of an A chain of 24 amino acids and a B chain of 29 amino acids.

Relaxin can be administered to an individual in the form of a polynucleotide comprising a nucleotide sequence which encodes relaxin. Relaxin-encoding nucleotide sequences are known in the art, any of which can be used in the methods described herein. See, e.g. GenBank Accession Nos. AF135824; AF076971; NM_006911; and NM_005059. The relaxin polynucleotides and polypeptides of the present invention can be introduced into a cell by a gene delivery vehicle. The gene delivery vehicle may be of viral or non-viral origin (see generally, Jolly, Cancer Gene Therapy (1994) 1:51-64; Kimura (1994) *Human Gene Therapy* 5:845-852; Connelly (1995) *Human Gene Therapy* 1:185-193; and Kaplitt (1994) *Nature Genetics* 6:148-153). Gene therapy vehicles for delivery of constructs including a coding sequence of a polynucleotide of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 415 731; WO 90/07936; WO 94/03622; WO 93/25698; WO 93/25234; U.S. Pat. No. 5, 219,740; WO 93/11230; WO 93/10218; Vile and Hart (1993) *Cancer Res.* 53:3860-3864; Vile and Hart (1993) *Cancer Res.* 53:962-967; Ram et al. (1993) *Cancer Res.* 53:83-88; Takamiya et al. (1992) *J. Neurosci. Res.* 33:493-503; Baba et al. (1993) *J. Neurosurg.* 79:729-735; U.S. Pat. No. 4,777,127; and EP 345,242.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Packaging cell lines are made from human (such as HT1080 cells) or mink parent cell lines, thereby allowing production of recombinant retroviruses that can survive inactivation in human serum.

Gene delivery vehicles can also employ parvovirus such as adeno-associated virus (AAV) vectors. Representative examples include the AAV vectors disclosed by Srivastava in WO 93/09239, Samulski et al. (1989) *J. Vir.* 63:3822-3828; Mendelson et al. (1988) *Virol.* 166:154-165; and Flotte et al. (1993) *Proc. Nat. Acad. Sci. USA* 90:10613-10617.

Also of interest are adenoviral vectors, e.g., those described by Berkner, Biotechniques (1988) 6:616-627; Rosenfeld et al.(1991) *Science* 252:431-434; WO 93/19191; Kolls et al. (1994) *Proc. Natl. Acad. Sci. USA* 91:215-219; Kass-Eisler et al. (1993) *Proc. Natl. Acad. Sci. USA* 90:11498-11502; WO 94/12649, WO 93/03769; WO 93/19191; WO 94/28938; WO 95/11984 and WO 95/00655.

Other gene delivery vehicles and methods may be employed, including polycationic condensed DNA linked or unlinked to killed adenovirus alone, for example Curiel (1992) *Hum. Gene Ther.* 3:147-154; ligand linked DNA, for example see Wu (1989) *J. Biol. Chem.* 264:16985-16987; eukaryotic cell delivery vehicles cells; deposition of photopolymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip (1994) *Mol. Cell Biol.* 14:2411-2418, and in Woffendin (1994) *Proc. Natl. Acad. Sci.* 91:1581-1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120; PCT Nos. WO 95/13796, WO 94/23697, and WO 91/14445; and EP No. 524 968.

Further non-viral delivery suitable for use includes mechanical delivery systems such as the approach described in Woffendin et al. (1994) *Proc. Natl. Acad. Sci. USA* 91:11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

In employing relaxin for increasing arterial compliance, any pharmaceutically acceptable mode of administration can be used. Relaxin can be administered either alone or in combination with other pharmaceutically acceptable excipients, including solid, semi-solid, liquid or aerosol dosage forms, such as, for example, tablets, capsules, powders, liquids, gels, suspensions, suppositories, aerosols or the like. Relaxin can also be administered in sustained or controlled release dosage forms (e.g., employing a slow release bioerodable delivery system), including depot injections, osmotic pumps (such as the Alzet implant made by Alza), pills, transdermal and transcutaneous (including electrotransport) patches, and the like, for prolonged administration at a predetermined rate, preferably in unit dosage forms suitable for single administration of precise dosages.

In some embodiments, relaxin is delivered using an implantable drug delivery system, e.g., a system that is programmable to provide for administration of relaxin. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for use in the present invention is the Synchromed infusion pump (Medtronic).

The compositions will typically include a conventional pharmaceutical carrier or excipient and relaxin. In addition, these compositions may include other active agents, carriers, adjuvants, etc. Generally, depending on the intended mode of administration, the pharmaceutically acceptable composition will contain about 0.1% to 90%, about 0.5% to 50%, or about 1% to about 25%, by weight of relaxin, the remainder being suitable pharmaceutical excipients, carriers, etc. Actual methods of preparing such dosage forms are known, or will be apparent, to those skilled in this art; for example, see Remington's Pharmaceutical Sciences, Mack Publishing Company, Easton, Pa., 15th Edition, 1995, or latest edition. The formulations of human relaxin described in U.S. Pat. No. 5,451,572, are non-limiting examples of suitable formulations which can be used in the methods of the present invention.

Parenteral administration is generally characterized by injection, either subcutaneously, intradermally, intramuscularly or intravenously, or subcutaneously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, and the like.

The percentage of relaxin contained in such parenteral compositions is highly dependent on the specific nature thereof, as well as the needs of the subject. However, percentages of active ingredient of 0.01% to 10% in solution are employable, and will be higher if the composition is a solid which will be subsequently diluted to the above percentages. In general, the composition will comprise 0.2-2% of the relaxin in solution.

Parenteral administration may employ the implantation of a slow-release or sustained-release system, such that a constant level of dosage is maintained. Various matrices (e.g., polymers, hydrophilic gels, and the like) for controlling the sustained release, and for progressively diminishing the rate of release of active agents such as relaxin are known in the art. See, e.g., U.S. Pat. No. 3,845,770 (describing elementary osmotic pumps); U.S. Pat. Nos. 3,995,651, 4,034,756 and 4,111,202 (describing miniature osmotic pumps); U.S. Pat. Nos. 4,320,759 and 4,449,983 (describing multichamber osmotic systems referred to as push-pull and push-melt osmotic pumps); and U.S. Pat. No. 5,023,088 (describing osmotic pumps patterned for the sequentially timed dispensing of various dosage units).

Drug release devices suitable for use in administering relaxin according to the methods of the invention may be based on any of a variety of modes of operation. For example, the drug release device can be based upon a diffusive system, a convective system, or an erodible system (e.g., an erosion-based system). For example, the drug release device can be an osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump, are also suitable for use with the present invention. Examples of such devices include those described in, for example, U.S. Pat. Nos. 4,692,147; 4,360,019; 4,487,603; 4,360,019; 4,725,852, and the like. In general, the present treatment methods can be accomplished using any of a variety of refillable, non-exchangeable pump systems. Osmotic pumps have been amply described in the literature. See, e.g., WO 97/27840; and U.S. Pat. Nos. 5,985,305 and 5,728,396.

Relaxin may be administered over a period of hours, days, weeks, months, or years, depending on several factors, including the degree of arterial stiffness, etc. For example, relaxin is administered for a period of time of from about 2 hours to about 8 hours, from about 8 hours to about 12 hours, from about 12 hours to about 24 hours, from about 24 hours to about 36 hours, from about 36 hours to about 72 hours, from about 3 days to about one week, from about 1 week to about 2 weeks, from about 2 weeks to about 1 month, from about 1 month to about 3 months, from about 3 months to about 6 months, from about 6 months to about 12 months, or from about 1 year to several years. The administration may be constant, e.g., constant infusion over a period of hours, days, weeks, months, years, etc. Alternatively, the administration may be intermittent, e.g., relaxin may be administered once a day over a period of days, once an hour over a period of hours, or any other such schedule as deemed suitable.

Formulations of relaxin may also be administered to the respiratory tract as a nasal or pulmonary inhalation aerosol or solution for a nebulizer, or as a microfine powder for insufflation, alone or in combination with an inert carrier such as lactose, or with other pharmaceutically acceptable excipients. In such a case, the particles of the formulation may advantageously have diameters of less than 50 micrometers, preferably less than 10 micrometers.

Combination Therapies

In some embodiments, a subject method is modified to include administration of at least one additional therapeutic agent. Suitable additional therapeutic agents include, but are not limited to, estrogen receptor modulators; anti-hypertensive agents such as calcium channel blockers, endothelin receptor antagonists, angiotensin-I converting enzyme (ACE) inhibitors, α-adrenergic blocking agents, vasodilators, diuretics, β-adrenergic blocking agents, renin inhibitors, and angiotensin receptor antagonists; natriuretic peptides (e.g., atrial natriuretic peptide, brain natriuretic peptide, and C-type natriuretic peptide); agents for blocking cholesterol production (e.g. statins) and agents used to treat diabetes.

Estrogen Receptor Modulators

Suitable estrogen receptor modulators include any of a variety of estrogen compounds, as well as Selective Estrogen Receptor Modulators ("SERMs"). SERMs include, but are not limited to, tamoxifen, raloxifen, droloxifene, idoxifene, lasofoxifene, CP-336,156, GW5638, LY353581, TSE-424, LY353381, LY117081, toremifene, fulvestrant, 4-[7-(2,2-dimethyl-1-oxopropoxy-4-methyl-2-[4-[2-(1-piperidinyl) ethoxy]phenyl]-2H-1-benzopyran-3-yl]-phenyl-2,2-dimethylpr-opanoate, 4,4'-dihydroxybenzophenone-2,4-dinitrophenyl-hydrazone, and SH646.

Suitable estrogen compounds include, but are not limited to, mestranol, an ester of estradiol, polyestriol phosphate, estrone sulfate, natural estrogens, synthetic estrogens, conjugated estrogens, estradiol, estradiol sulfamates, estradiol valerate, estradiol benzoate, ethinyl estradiol, estrone, estriol, estriol succinate and conjugated estrogens, aconjugated equine estrogen, estrone sulfate, 17β-estradiol sulfate, 17α-estradiol sulfate, equilin sulfate, 17βdihydroequilin sulfate, 17α-dihydroequilin sulfate, equilenin sulfate, 17β-dihydroequilenin sulfate and 17α-dihydroequilenin sulfate.

Also suitable for use are micronized forms of estrogens, such as micronized estradiol, micronized estradiol sulfamates, micronized estradiol valerate, micronized estradiol benzoate, micronized estrone, or micronized estrone sulfate or mixtures thereof, notably micronized estradiol, micronized estradiol valerate, micronized estradiol benzoate or micronized estradiol sulfamates.

Effective dosages of estrogens are conventional and well known in the art. Typical approximate dosages for oral administration are, e.g., ethinyl estradiol (0.001-0.030 mg/day), mestranol (5-25 mcg/day), estradiol (including 17.beta. estradiol), (0.5-6 mg/day), polyestriol phosphate (2-8 mg) and conjugated estrogens (0.3-1.2 mg/day). Dosages for other means of delivery will be evident to one of skill in the art. For example, transdermal dosages will vary therefrom in accordance with the adsorption efficacy of the vehicle employed.

Estrogen compounds can be administered by any of a variety of conventional modes, including, e.g., oral (e.g., solutions, suspensions, tablets, dragees, capsules or pills), parenteral (including subcutaneous injection, or intravenous, intramuscular or intrastemal injection or infusion techniques), inhalation spray, transdermal, rectal, or vaginal (e.g., by vaginal rings or creams) administration.

Anti-hypertensive Agents

Suitable ACE inhibitor include, but are not limited to, benazepril (Lotensin®), captopril (Capoten®), enalapril, enalaprilat, fosinopril (Monopril®), lisinopril (Zestril®; Prinivil®,), pentopril, quinapril (Accupril®), quinaprilat, ramipril (Altace®), trandolapril (Mavik®), zofenopril, moexipril (Univasc®), perindopril (Coversyl®; Aceon®), Vasotec®, cilazapril (Inhibace®).

Suitable diuretics include, but are not limited to, acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; ticrynafen; triamterene; and trichlormethiazide.

Suitable α-adrenergic blocking agents include, e.g., dibenamine; phentolamine; phenoxybenzamine; prazosin; prazosin/polythiazide (Minizide®); tolazoline; doxazosin (Cardura); terazosin (Hytrin®); tamsulosin (Flomax®); and alfuzosin (Uroxatral®).

Suitable β-adrenergic blocking agents include, but are not limited to, Betapace (sotalol), Blocadren (timolol), Brevibloc (esmolol), Cartrol (carteolol), Coreg (carvedilol), Corgard (nadolol), Inderal (propranolol), Inderal-LA (propranolol), Kerlone (betaxolol), Levatol (penbutolol), Lopressor (metoprolol), Normodyne (labetalol), Sectral (acebutolol), Tenormin (atenolol), Toprol-XL (metoprolol), Trandate (labetalol), Visken (pindolol), and Zebeta (bisoprolol).

Suitable vasodilators include, but are not limited to, diazoxide, hydralazine (Apresoline®), minoxidil, nitroprusside (Nipride®), sodium nitroprusside, diazoxide (Hyperstat IV), verapamil, and nefidipine.

Suitable calcium channel blockers include, but are not limited to, amlodipine (Norvasc®), felodipine (Plendil®), nimodipine, isradipine, nicardipine, nifedipine (Procardia®), bepridil (Vascor®), diltiazem (Cardiazem®), and verapamil (Isoptin®; Calan®).

Suitable angiotensin II receptor blockers or inhibitors include, but are not limited to, saralasin, losartan (Cozaar), ciclosidomine, eprosartan, furosemide, irbesartan, and valsartan.

Suitable renin inhibitors include, e.g., pepstatin and the di- or tripeptide renin inhibitors; enalkrein, RO 42-5892 (Hoffman LaRoche), A 65317 (Abbott), CP 80794, ES 1005, ES 8891, SQ 34017; a compound as disclosed in U.S. Pat. No. 6,673,931; and the like.

Suitable endothelin antagonists useful in the present invention include, but are not limited to, atrasentan (ABT-627; Abbott Laboratories), Veletri™ (tezosentan; Actelion Pharmaceuticals, Ltd.), sitaxsentan (ICOS-Texas Biotechnology), enrasentan (GlaxoSmithKline), darusentan (LU135252; Myogen) BMS-207940 (Bristol-Myers Squibb), BMS-193884 (Bristol-Myers Squibb), BMS-182874 (Bristol-Myers Squibb), J-104132 (Banyu Pharmaceutical), VML 588/Ro 61-1790 (Vanguard Medica), T-0115 (Tanabe Seiyaku), TAK-044 (Takeda), BQ-788 (Banyu Pharmaceutical), BQ123, YM-598 (Yamanouchi Pharma), PD 145065 (Parke-Davis), A-127722 (Abbott Laboratories), A-192621 (Abbott Laboratories), A-182086 (Abbott Laboratories), TBC3711 (ICOS-Texas Biotechnology), BSF208075 (Myogen), S-0139 (Shionogi), TBC2576 (Texas Biotechnology), TBC3214 (Texas Biotechnology), PD156707 (Parke-Davis), PD180988 (Parke-Davis), ABT-546 (Abbott Laboratories), ABT-627 (Abbott Laboratories), SB247083 (GlaxoSmith-Kline), SB 209670 (GlaxoSmithKline); and an endothelin receptor antagonists discussed in the art, e.g., Davenport and Battistini (2002) *Clinical Science* 103:15-35, Wu-Wong et al. (2002) *Clinical Science* 103:1075-1115, and Luescher and Barton (2000) *Circulation* 102:2434-2440. A suitable endothelin receptor antagonist is TRACLEER™ (bosentan; manufactured by Actelion Pharmaceuticals, Ltd.). TRACLEER™ is an orally active dual endothelin receptor antagonist, and blocks the binding of endothelin to both of its receptors endothelin receptor A and endothelin receptor B. TRACLEER™ is generally administered at a dose of 62.5 mg bid orally for 4 weeks, followed by a maintenance dose of 125 mg bid orally.

Other suitable antihypertensive agents include, e.g., aminophylline; cryptenamine acetates and tannates; deserpidine; meremethoxylline procaine; pargyline; clonidine (Catapres); methyldopa (Aldomet); reserpine (Serpasil); guanethidine (Ismelin); and tirmethaphan camsylate.

Statins

Suitable statins include, without limitation, products such as Crestor, Lipitor, Lescol, Mevacor, Pravochol, Zocor and related compounds such as those discussed, e.g., in *Rev. Port. Cardio.* (2004) 23(11):1461-82; Curr Vasc Pharmacol. (2003) 3:329-33.

Therapeutic Agents for Treating Type 1 or Type 2 Diabetes

Other suitable agents for use in a combination therapy with relaxin include therapeutic agents for treating Type I diabetes, and therapeutic agents for treating Type 2 diabetes (e.g., agents that increase insulin sensitivity).

Insulin

Therapeutic agents for treating Type 1 diabetes include any form of insulin, as long as the insulin is biologically active, i.e., the insulin is effective in reducing blood glucose levels in an individual who is responsive to insulin. In some embodiments, recombinant human insulin ("regular" insulin) or a recombinant human insulin analog is used. In a particular embodiment, the insulin analog is a monomeric form of insulin, e.g., human lispro. In some instances, other forms of insulin are used alone or in combination with recombination human insulin or each other. Insulin that is suitable for use herein includes, but is not limited to, regular insulin (Humulin R, Novlin R, etc.), semilente, NPH (isophane insulin suspension; Humulin N, Novolin N, Novolin N PenFill, NPH Ilentin II, NPH-N), lente (insulin zinc suspension; Humulin-L, Lente Ilentin II, Lent L, Novolin L), protamine zinc insulin (PZi), ultralente (insulin zinc suspension, extended; Humulin U Ultralente), insuline glargine (Lantus), insulin aspart (Novolog), acylated insulin, monomeric insulin, superactive insulin, hepatoselective insulin, lispro (Humalog™), and any other insulin analog or derivative, and mixtures of any of the foregoing. Commonly used mixtures include mixtures NPH and regular insulin containing the following percentages of NPH and regular insulin: 70%/30%, 50%/50%, 90%/10%, 80%/20%, 60%/40%, and the like. Insulin that is suitable for use herein includes, but is not limited to, the insulin forms disclosed in U.S. Pat. Nos. 4,992,417; 4,992,418; 5,474,978; 5,514,646; 5,504,188; 5,547,929; 5,650,486; 5,693,609; 5,700,662; 5,747,642; 5,922,675; 5,952,297; and 6,034,054; and published PCT applications WO 00/121197; WO 90/10645; and WO 90/12814. Insulin analogs include, but are not limited to, superactive insulin analogs, monomeric insulins, and hepatospecific insulin analogs.

Superactive insulin analogs have increased activity over natural human insulin. Accordingly, such insulin can be administered in substantially smaller amounts while obtaining substantially the same effect with respect to reducing serum glucose levels. Superactive insulin analogs include, e.g., 10-Aspartic Acid-B human insulin; des-pentapeptide (B26-B30)→Asp$^{B10}$, Tyr$^{B25}$-α-carboxamide human insulin; (B26-B30)→glu$^{B10}$, Tyr$^{B25}$-α-carboxamide human insulin; destripeptide B28-30 insulin; an insulin with γ-aminobutyric acid substituted for A13Leu-A14Tyr; and further insulin analogs of the formula des(B26-B30)→X$^{B10}$, Tyr$^{B25}$-α-carboxamide human insulin, in which X is a residue substituted at position 10 of the B chain. These insulin analogs have potencies anywhere from 11 to 20 times that of natural human insulin. All of the above-described insulin analogs involve amino acid substitutions along the A or B chains of natural human insulin, which increase the potency of the compound or change other properties of the compound. Monomeric insulin includes, but is not limited to, lispro.

Insulin derivatives include, but are not limited to, acylated insulin, glycosylated insulin, and the like. Examples of acylated insulin include those disclosed in U.S. Pat. No. 5,922,675, e.g., insulin derivatized with a $C_6$-$C_{21}$ fatty acid (e.g., myristic, pentadecylic, palmitic, heptadecylic, or stearic acid) at an α- or ε-amino acid of glycine, phenylalanine, or lysine.

Agents that Increase Insulin Sensitivity

In some embodiments, a subject treatment regimen for treating an individual with Type 2 diabetes further comprises administering an additional agent that reduces insulin resistance (e.g., increases insulin sensitivity). Suitable agents that treat insulin resistance include, but are not limited to, a biguanide such as Metformin (e.g., administered in an amount of 500 mg or 850 mg three times per day), Phenformin, or a salt thereof; a thiazolidinedione compound such as troglitazone (see, e.g., U.S. Pat. No. 4,572,912), rosiglitazone (Smith-KlineBeecham), pioglitazone (Takeda), Glaxo-Welcome's GL-262570, englitazone (CP-68722, Pfizer) or darglitazone (CP-86325, Pfizer, isaglitazone (MCC-555; Mitsubishi; see, e.g., U.S. Pat. No. 5,594,016), reglitazar (JTT-501), L-895645 (Merck), R-119702 (Sankyo/WL), NN-2344, YM-440 (Yamanouchi), Ragaglitazar (NNC 61-0029 or DRF2725; NovoNordisk), farglitazar (GI262570), tesaglitazar (AZ 242), KRP-297, and the like; and combinations such as Avandamet™ (rosiglitazone maleate and metformin-HCl).

Subjects Suitable for Treatment

Individuals who are suitable for treatment with a subject method include any individual having arterial stiffness (or reduced arterial compliance) for any reason. Such individuals include individuals having a disorder that is associated with or results from, reduced arterial compliance, including, but not limited to, atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiff niess associated with age, systemic lupus erythematosus, preeclampsia, and hypercholesterolemia.

Particularly suitable for treatment are individuals whose measured global arterial compliance is decreased relative to a similarly situated healthy individual. Also particularly suitable for treatment are individuals with a measured local arterial compliance which is decreased relative to the local arterial compliance expected in a similarly situated healthy individual. Individuals with a measured regional arterial compliance which is decreased relative to that expected in a similarly healthy individuals are also particularly suitable for treatment. In some instances, the global, local or regional arterial compliance of an individual at different points in time may be measured and compared to determine whether the arterial compliance in that individual is decreasing and approaching levels which indicate that intervention is appropriate.

Individuals who are suitable for treatment with a subject method include individuals who have developed, or who are at risk of developing, age-associated arterial stiffness. Such individuals include humans who are over the age of 50 years, e.g., humans who are from about 50 years old to about 60 years old, from about 60 years old to about 65 years old, from about 65 years old to about 70 years old, from about 70 years old to about 75 years old, from about 75 years old to about 80 years old, or older.

Also suitable for treatment with a subject method are peri-menopausal women, menopausal women, postmenopausal women, and women who have ceased menstruation for non-age-related reasons, e.g., as a result of surgery (e.g., hysterectomy, oophorectomy), and thus have developed, or are at risk of developing, arterial stiffness. Such women can be treated with a combination therapy involving relaxin and estrogen. Such women can also be treated with a combination therapy involving relaxin, estrogen, and an anti-hypertensive agent.

Also suitable for treatment with a subject method are individuals who have been diagnosed with Type 1 diabetes mellitus. Also suitable for treatment with a subject method are individuals who have been diagnosed with Type 2 diabetes mellitus. Individuals who are insulin resistant are identified by one or more of the following criteria: 1) a HOMA-IR value that is greater than 2.5 (based on the calculation fasting insulin (mU/ml)×fasting glucose (mmol/l)/22.5); 2) a fasting serum insulin level of greater than about 20 µU/mL, or greater than about 25 µU/mL; 3) a fasting serum C-peptide level of greater than about 3.5 ng/mL, or greater than about 4.5 ng/mL.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Effect of Relaxin on Systemic Arterial Resistance and Compliance

Methods

Animals

Long-Evans female rats of 12-14 weeks old were purchased from Harlan Sprague-Dawley (Frederick, Md. USA). They were provided PROLAB RMH 2000 diet containing 0.48% sodium (PME Feeds Inc., St. Louis, Mo. USA) and water ad libitum. The rats were maintained on a 12 h light/dark cycle. The Institutional Animal Care and Use Committee of the Magee-Womens Research Institute approved all animal procedures.

Surgical Preparation

Briefly, the rats were habituated to Nalgene metabolism cages for one week (VWR Scientific Products), followed by further habituation to a harness/7.5 cm spring assembly for another week while in the metabolism cage (Harvard Apparatus, Holliston, Mass. USA). The animals were fitted to the harness under isofluorane anesthesia. After this habituation period, the rats were anesthetized with 60 mg/kg ketamine i.m. and 21 mg/kg pentobarbital i.p., and placed in the prone position on a heating pad. After application of 70% ethanol and betadine to all exposed skin areas, ampicillin was administered s.c. (0.2 ml of a 125 mg/ml solution) and atropine was also administered s.c. (0.075 ml of a 0.4 mg/ml solution). Next, a sterile tygon catheter (18 in long, 0.015 in ED, 0.030 OD) connected to a syringe containing Ringer's solution, as well as a sterile thermodilution microprobe (22 cm long, F #1.5; Columbus Instruments, Columbus, Ohio USA) were threaded through the spring. The tygon catheter was subsequently threaded through the hole in the harness and then tunneled subcutaneously from the midpoint between the shoulder blades out the small incision behind the ear using an 18-gauge trocar.

The thermodilution catheter was also threaded through the harness assembly and then tunneled subcutaneously from the midpoint between the scapulae out the skin incision in the left costal margin. The spring was then reattached to the harness. The rat was repositioned on the back. A 1.0 cm skin incision was made in the left inguinal region. The external iliac artery was isolated and prepared for catheterization. The thermocouple was then tunneled subcutaneously exiting at the inguinal incision. The thermocouple was next inserted into the external iliac artery being directed rostrally, so that it passed. easily into the internal iliac artery and subsequently into the aorta. At the 4.0 cm, the thermocouple lay approximately 1.0 cm below the left renal artery. Next, a horizontal 2.0 cm incision was made over the trachea, 1.0 cm above the cricoid notch.

Through this incision, a large subcutaneous pocket was dissected in the neck and above the left shoulder. The right jugular vein and carotid artery were then isolated and prepared for catheterization, the latter facilitated by placing a small roll of gauze under the neck to elevate this deep structure. Using the 18-gauge trocar, the tygon catheter was tunneled subcutaneously from the small incision behind the right ear out the incision in the neck. The tygon catheter was implanted in the right jugular vein 3.0 cm, thereby placing the catheter tip at the confluence of the anterior vena cava and the right atrial appendage. The battery/transmitter of a sterile mouse pressure catheter (TA11PA-C20; ca. F #1.2; Data Sciences International, St. Paul, Minn. USA) was inserted in the subcutaneous pocket. The mouse pressure catheter was then implanted in the right carotid artery 2.8 cm, thereby placing the catheter tip at the confluence of the right carotid artery and aortic arch. All wounds were closed with 4-0 silk or autoclips. After instilling 0.05 ml of a heparin solution into the jugular catheter and plugging it with a straight pin, the rat was placed in the metabolism cage and given ampicillin by drinking water for 2 days (100 mg/50 ml with 2 tablespoons of dextrose). The spring and catheters that exit the cage top were secured.

Terbutrol was given s.c. for post-operative analgesia as soon as the rats were recovered sufficiently from the anesthesia. For low dose administration of recombinant human relaxin (4.0 μg/h rhRLX) for 10 days, two Alzet model 2002 osmotic minipumps (Durect Corporation, Curpertino, Calif. USA) were inserted subcutaneously in the back of the animal under isoflurane anesthesia. For high dose administration for 10 days (25 μg/h), one Alzet model 2ML2 osmotic minipump was implanted. After completion of the measurement for the last time point, the rat was anesthetized with 60 mg/kg pentobarbital i.v. Blood was obtained from the abdominal aorta for rhRLX levels, osmolality and hematocrit. The position of the jugular catheter relative to the right atrium, the placement of the pressure catheter relative to the aortic arch, and the position of the thermocouple relative to the left renal artery were recorded.

In Vivo Studies: Hemodynamics and Systemic Arterial Mechanical Properties

Time control studies were first performed in 5 rats, in order to document the stability of systemic hemodynamics over a 17 day period after surgery. Measurements were recorded on days 4-5, 7-8, 9-10, 13-14, and 16-17 after surgery. The low and high dose rhRLX protocols entailed 6 and 7 rats, respectively. In addition, the vehicle for rhRLX (20mM sodium acetate, pH 5.0) was administered to another 6 rats. After 2 baseline measurements of systemic hemodynamics on days 5 and 7 after surgery, either low or high dose rhRLX or vehicle was administered by osmotic minipump. Systemic hemodynamics were again assessed on days 3, 6, 8 and 10 after initiation of rhRLX or vehicle infusion.

Each measurement consisted of 4 to 6 recordings of cardiac output and blood pressure waveforms that were obtained when the rat was either sleeping or resting. At least 10 min was allowed between recordings. These measurements were obtained between 9 am and 3 pm.

Cardiac Output. To measure cardiac output, we used the thermodilution technique. Osborn et al. (1986) *Am. J. Physiol.* 251:H1365-H1372. Ringer's solution of known volume and temperature was injected into the anterior vena cava using the Micro Injector 400 (Columbus Instruments). The cardiac output was calculated from the change in blood temperature (Cardiotherm 400R, Columbus Instruments). The cardiac output as determined by the Cardiotherm 400R was calculated as:

$CO=[(B_T-I_T)*V_I]/\int B_T(t)$ where, $B_T$ is the blood temperature (recorded by the thermocouple implanted in the abdominal aorta), $I_T$ is the injectate temperature (room temperature), $V_I$ is the injectate volume (150 μL), and $B_T(t)$ is the blood temperature as a function of time.

Blood Pressure. Instantaneous aortic pressure was recorded using a blood pressure telemetry system (Data Sciences International, St. Paul, Minn. USA). Mills et al. (2000) *J. Appl. Physiol.* 88:1537-1544. The aortic pressure was recorded by a pressure catheter implanted in the aortic arch via the right carotid artery and transmitted to an external receiver. Steady-state aortic pressure was digitized online using a PC-based data acquisition system with 16 bit resolution and 2000 Hz sampling rate and stored as text files for off-line analysis. Each measurement consisted of a 30 second sampling duration.

Aortic Pressure Analysis. Analysis of the acquired data and calculation of global AC was performed by a custom computer program developed using MATLAB software (MathWorks Inc., Natick, Mass. USA). Briefly, individual beats were selected (3-15 cycles) from the 10 seconds of the aortic pressure recording, immediately preceding the measurement of cardiac output. The ensemble was averaged as described by Burattini et al. ((1985) *Comput. Biomed. Res.* 18:303-312) to yield a single representative beat for each trial. The mean arterial pressure (MAP), peak systolic pressure ($P_s$), and end diastolic pressure ($P_d$) were calculated from this averaged beat. Pulse pressure (PP) was calculated as $P_s$-$P_d$. Systemic vascular resistance (SVR) was calculated by dividing the MAP by CO.

Global Arterial Compliance. Two measures of global arterial compliance were calculated. The first ($AC_{area}$) was calculated from the diastolic decay of the aortic pressure waveform [P(t)] using the area method (2): $AC_{area}=A_d/[SVR(P_1-P_2)]$ where $P_1$ and $P_2$ are the pressures at the beginning and end of the diastolic decay curve, respectively, and $A_d$ is the area under the P(t) waveform over this region. The second measure of global arterial compliance was calculated as the stroke volume-to-pulse pressure ratio (Chemla et al. (1998) *Am. J. Physiol.* 274:H500-H505). Stroke volume was defined as CO/HR.

In Vitro Studies: Arterial Passive Mechanics

Nonpregnant female rats were administered rhRLX (4 /μ/h) or vehicle by osmotic minipump for 5 days. A kidney was removed and placed in ice-cold HEPES buffered physiological saline solution (PSS, a modified Kreb's buffer). The HEPES-physiologic saline solution was composed of (in mmol/L): sodium chloride 142, potassium chloride 4.7, magnesium sulfate 1.17, calcium chloride 2.5, potassium phosphate 1.18, HEPES 10, glucose 5.5, and was pH 7.4 at 37° C. A stereo dissecting microscope, fine forceps and iridectomy scissors were used to isolate interlobar arteries as described by Gandley et al. ((2001) *Am. J. Physiol.* 280:R1-R7) (unpressurized inner diameter, 100-200 μm). An arterial segment was then transferred to an isobaric arteriograph (Living Systems Instrumentation, Burlington, Vt. USA) and mounted on 2 glass micro-cannulae suspended in the chamber. After the residual blood was flushed from the lumen of the artery, the distal cannula was occluded to prevent flow. The proximal cannula was attached to a pressure transducer, a pressure servo-controller and a peristaltic pump. The servocontroller maintained a selected intraluminal pressure that was changed in a stepwise manner. An electronic dimension analyzing system obtained arterial diameter measures.

The vessels were incubated in the bath with $10^{-4}$ M papaverine and $10^{-2}$ M EGTA in calcium-free HEPES PSS. After a 30 min equilibration period, transmural pressure was increased in 14 steps beginning at 0 mmHg up to 150 mmHg. Inner and outer diameters as well as wall thickness were measured following each pressure step when the vessel had reached a steady state. Midwall radius ($R_m$) and circumferential wall stress ($\sigma$) were calculated from these data as described before (Cholley et al. (2001) *J. Appl. Physiol.* 90:2427-2438). Vessel wall elastic properties were quantified in terms of the incremental elastic modulus ($E_{inc}$), which was calculated from the $\sigma$-$R_m$ relationship (Pagani et al. (1979) *Circ. Res.* 44:420-429).

Serum Measurements

Serum osmolality was measured using a freezing-point depression instrumentation osmometer (Model 3 MO; Advanced Instruments, Needham Heights, Mass. USA). The levels of rhRLX in serum were measured by a quantitative sandwich immunoassay as previously described (Jeyabalan et al. (2003) *Circ Res.* 93(12): 1249-57).

Preparation of rhRLX

Two model 2002 osmotic minipumps (Durect Corporation, Cupertino, Calif. USA) were used to deliver the rhRLX for 10 days at the dose of 4 μg/h which yielded concentrations of circulating relaxin similar to those measured during early to midgestation in rats, i.e., 10-20 ng/ml when pregnancy-induced renal vasodilation is maximal in this species. One model 2ML2 osmotic minipump was used to deliver rhRLX at the dose of 25 μg/h for 10 days which we expected to produce concentrations of circulating hormone comparable to those recorded during mid to late gestation when further increases in CO and decreases in SVR are observed in this species. The rhRLX (Connetics, Palo Alto, Calif. USA) provided as a 5.0 mg/ml solution in 20 mM sodium acetate, pH 5.0 was diluted in the same buffer.

Statistical Analysis

Data are presented as means+SEM. One or two-factor repeated-measures ANOVA (Zar (1984) Biostatistical Analysis, Englewood Cliffs, N.J.:Prentice Hall) was used to compare mean values among various groups. If significant main effects or interactions were observed, comparisons between groups were performed using Fisher's LSD or Dunnett's test. The student's paired 't' test was used to compare the composite mean values during infusion of rhRLX (i.e., values averaged over all time points during rhRLX infusion) with baseline. Least squares regression analysis was performed on $\sigma$-$R_m$ and $E_{inc}$-$R_m$ relationships. Analysis of excess variance (or extra sum of squares) was used to compare these relationships between vehicle and relaxin-treated groups. $P<0.05$ was taken to be significant.

Results

In Vivo Studies

Time control. The stability of systemic arterial hemodynamics and load over a 17-day period after surgery in control rats (Table 1). Heart rate declined significantly due to a training effect as previously reported (Conrad and Russ (1992) *Am. J. Physiol.* 31 :R472-477). Stroke volume reciprocally increased, such that CO was unchanged. All other variables did not change significantly over the 17-day period after surgery, thus this conscious rat model can be used to obtain meaningful data under the experimental conditions described next (Table 1).

TABLE 1

| | Time Control Rats | | | | | | |
|---|---|---|---|---|---|---|---|
| Time After Surgery (days) | $\Delta_T$ (° C.) | CO (mL/min) | HR* (bpm) | SV* (mL) | $AC_{area}$ (μl/mmHg) | SVR (mmHg.s/mL) | MAP (mmHg) |
| 4-5 | 0.37 ± 0.01 | 119 ± 3 | 428 ± 7 | 0.28 ± 0.01 | 6.8 ± 0.3 | 57 ± 2 | 107.6 ± 0.8 |
| 7-8 | 0.37 ± 0.01 | 121 ± 3 | 378 ± 8 | 0.32 ± 0.01 | 7.2 ± 0.3 | 55 ± 2 | 107.3 ± 1.5 |
| 9-10 | 0.38 ± 0.01 | 120 ± 4 | 382 ± 8 | 0.31 ± 0.01 | 6.9 ± 0.3 | 55 ± 2 | 108.1 ± 1.5 |
| 13-14 | 0.35 ± 0.01 | 115 ± 4 | 354 ± 5 | 0.32 ± 0.01 | 7.3 ± 0.3 | 58 ± 2 | 107.0 ± 1.5 |
| 16-17 | 0.32 ± 0.02 | 122 ± 3 | 349 ± 7 | 0.36 ± 0.01 | 8.0 ± 0.4 | 52 ± 2 | 103.7 ± 2.2 |

Mean±SEM. N=5 rats. $\Delta_T$, change in blood temperature after injection of Ringer's solution into the right heart; CO, cardiac output; HR, heart rate; SV, stroke volume; $AC_{area}$, global arterial compliance calculated using area method; SVR, systemic vascular resistance; MAP, mean arterial pressure.
*$P<0.05$ by single factor repeated measures ANOVA.

Figure 2:
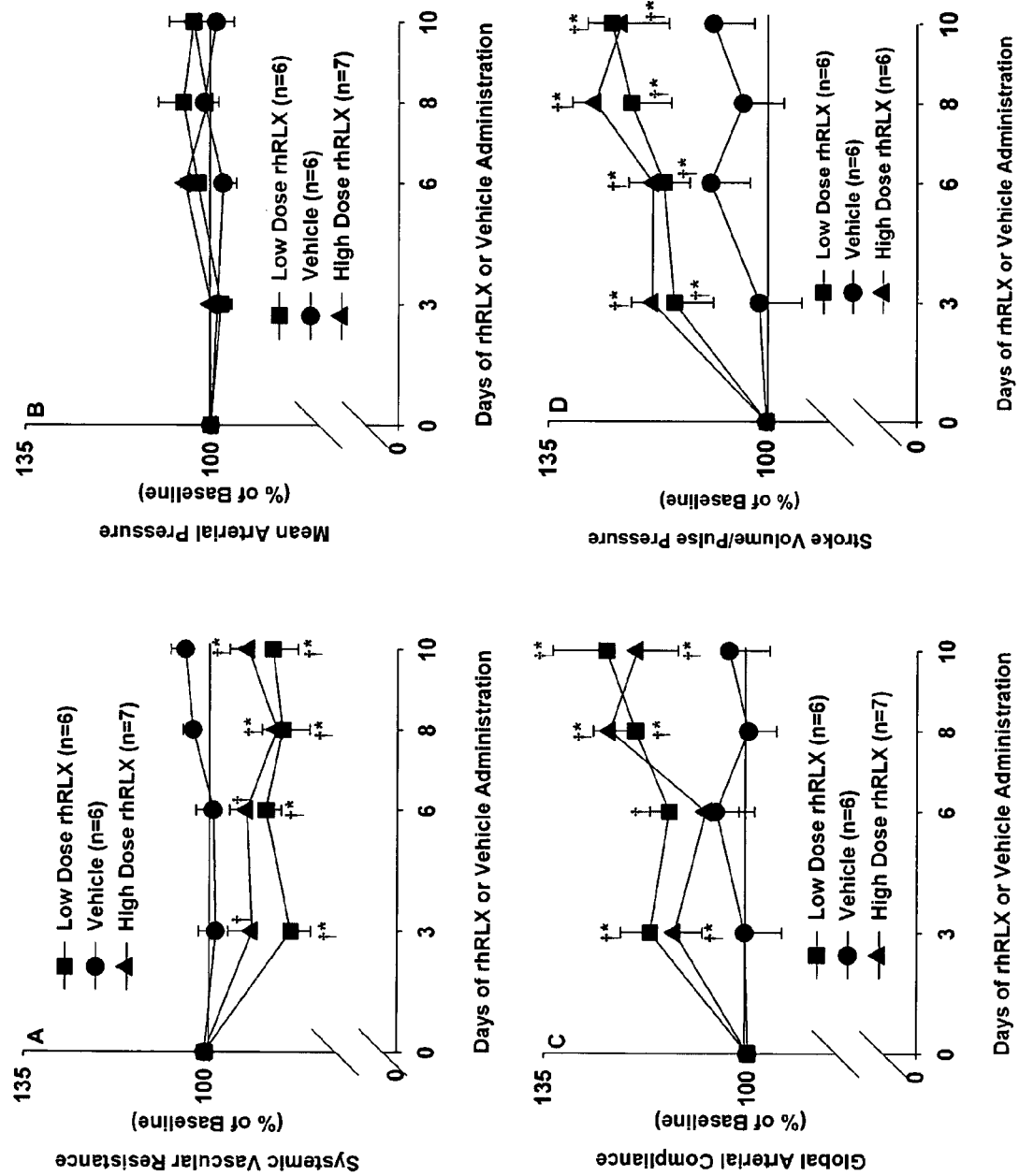
FIGS. 2A-D depict percent change from baseline for systemic vascular resistance (FIG. 2A), mean arterial pressure (FIG. 2B), global arterial compliance (FIG. 2C), and ratio of stroke volume-to-pulse pressure in female rats administered low dose rhRLX, high dose rhRLX, or vehicle.

Rats administered vehicle (for rhRLX J. These results were derived from 3 rats administered the vehicle for rhRLX at the infusion rate of 1 μl/h, and from another 3 rats administered the vehicle for rhRLX at the infusion rate of 5 μl/h. (These correspond to the flow rates for the low and high dose administration of rhRLX, respectively.) The results were comparable, and therefore, combined. FIGS. 1 and 2 depict the percent change from baseline for systemic hemodynamics and other variables. Similar to the time control studies, there was a significant decrease in heart rate, which was offset by an insignificant rise in stroke volume, such that CO remained unchanged. All other variables remained relatively constant. Combining all of the time points during administration of vehicle yielded overall changes in CO, global AC, and SVR of −1.4+1.3, 2.2+4.6, and 0.4 +3.4% of baseline, respectively (all P NS vs. baseline). As expected, there was no measurable rhRLX in the serum, and the osmolality was 309+6 mOsm/kg water.

Rats administered low dose rhRLX(4 μg/h). The absolute values for systemic hemodynamics and other parameters are shown in Table 2, while FIGS. 1 and 2 show the temporal pattern of percentage change from baseline.

TABLE 2

Rats Administered Low Dose rhRLX (4 μg/h)

| Days After Minipump | $\Delta_T$ (°C.) | CO* (mL/min) | HR (bpm) | SV* (mL) | $AC_{area}$* (μl/mmHg) | SVR* (mmHg.s/mL) | MAP (mmHg) |
|---|---|---|---|---|---|---|---|
| Baseline | 0.34 ± 0.02 | 128 ± 2 | 417 ± 6 | 0.31 ± 0.01 | 6.2 ± 0.3 | 51 ± 2 | 111.6 ± 3.7 |
| 2-3 | 0.31 ± 0.01 | 151 ± 6 | 436 ± 9 | 0.35 ± 0.01 | 7.2 ± 0.3 | 43 ± 3 | 110.2 ± 4.9 |
| 6 | 0.31 ± 0.01 | 149 ± 7 | 419 ± 6 | 0.36 ± 0.02 | 7.1 ± 0.5 | 46 ± 3 | 116.9 ± 3.8 |
| 8 | 0.31 ± 0.01 | 159 ± 7 | 427 ± 11 | 0.37 ± 0.02 | 7.4 ± 0.5 | 44 ± 2 | 112.1 ± 2.8 |
| 10 | 0.31 ± 0.01 | 153 ± 5 | 418 ± 10 | 0.37 ± 0.01 | 7.7 ± 0.5 | 44 ± 2 | 115.2 ± 5.8 |

Mean±SEM. N=6 rats. Two baseline measurements were made on days 5 and 7 after surgery. These results were averaged for each rat. For abbreviations, see Table 1.

Low dose rhRLX significantly increased CO relative to baseline and to vehicle infusion (FIG. 1A). The infusion of rhRLX prevented the decline normally observed in HR (c.f vehicle, FIG. 1B), and the hormone significantly increased SV (FIG. 1C). Thus, increases in both SV and HR combined to raise the CO relative to vehicle-infused rats. Systemic vascular resistance fell significantly relative to baseline and vehicle infusion (FIG. 2A), while MAP remained unchanged (FIG. 2B).

Global AC significantly increased relative to baseline and vehicle infusion (FIG. 2C). There was no significant change in pulse pressure; however, the ratio of stroke volume-to-pulse pressure, another index of arterial compliance, increased significantly during the infusion of low dose rhRLX relative to baseline and to vehicle infusion (FIG. 2D). The time course of changes in variables that showed a significant change with low dose rhRLX administration (i.e., significant F value for relaxin and/or interaction), was further examined. By post hoc pairwise comparisons of data at different time points (Fisher's LSD). Both CO and SV were significantly higher than baseline at day 3. While SV continued to increase until day 8 (P<0.05, day 8 vs. day 3) (FIG. 1C), there were no significant changes with time in CO beyond day 3 (FIG. 1A). This was a result of a small, but insignificant, fall in HR from day 3 to day 8 (FIG. 1B).

SVR and both measures of global AC were significantly altered at day 3; thereafter there were no further significant changes (FIG. 2). In general, maximal changes in arterial hemodynamics and mechanical properties following low dose rhRLX administration were observed at the earliest time point examined (day 3), with no further temporal alterations. Combining all of the time points during administration of low dose rhRLX yielded an overall increase in CO and global AC of 19.2+4.8 and 21.4+3.6% above baseline, respectively, and an overall decrease in SVR of 15.5+2.4% below baseline (all P<0.01 vs. baseline). Serum rhRLX and osmolality were 14+2 ng/ml and 284+2 mOsm/kg water, respectively. The latter significantly decreased compared to vehicle infusion.

Rats Administered High Dose rhRLX(25 μg/h). The absolute values for systemic hemodynamics and other variables are presented in Table 3, and FIGS. 1 and 2 portray the percent change from baseline. The results for the high dose infusion were comparable to the low dose administration in direction, but somewhat less in magnitude.

TABLE 3

Rats Administered High Dose rhRLX (25 μg/h)

| Days After Minipump | $\Delta_T$ (°C.) | CO* (mL/min) | HR (bpm) | SV (mL) | $AC_{area}$* (μl/mmHg) | SVR* (mmHg.s/mL) | MAP (mmHg) |
|---|---|---|---|---|---|---|---|
| Baseline | 0.37 ± 0.02 | 129 ± 6 | 438 ± 10 | 0.30 ± 0.02 | 7.7 ± 0.7 | 53 ± 3 | 111.6 ± 3.7 |
| 2-3 | 0.33 ± 0.02 | 141 ± 7 | 454 ± 13 | 0.31 ± 0.02 | 8.5 ± 0.8 | 49 ± 4 | 110.2 ± 4.9 |
| 6 | 0.35 ± 0.02 | 147 ± 4 | 432 ± 10 | 0.34 ± 0.01 | 8.1 ± 0.4 | 48 ± 2 | 116.9 ± 3.8 |
| 8 | 0.35 ± 0.03 | 150 ± 5 | 451 ± 9 | 0.33 ± 0.01 | 9.4 ± 0.7 | 45 ± 2 | 112.1 ± 2.8 |
| 10 | 0.34 ± 0.02 | 146 ± 9 | 442 ± 6 | 0.33 ± 0.02 | 9.2 ± 1.0 | 48 ± 3 | 115.2 ± 5.8 |

Mean±SEM. N=7 rats. Two baseline measurements were made on days 5 and 7 after surgery. These results were averaged for each rat. For abbreviations, see Table 1.

The temporal analysis of changes in individual variables with high dose rhRLX was performed in a manner similar to that for the low dose rhRLX. Once again, CO (FIG. 1A), SV (FIG. 1C), SVR (FIG. 2A), and global AC (SV/PP method) (FIG. 2D) were maximally altered by the earliest time point examined (day 3), with no further significant changes thereafter. The temporal response of global AC as calculated by the area method (FIG. 2C) deviated slightly from this general pattern—$AC_{area}$ at day 6 was not different from that at baseline. This is likely an aberrant measurement because the second measure of global AC at all time points (FIG. 2D) and $AC_{area}$ at days 3, 8, and 10 (FIG. 2C) were significantly higher than baseline. Combining all of the time points during administration of high dose rhRLX yielded an overall increase in CO and global AC of 14.1+3.2 and 15.6+4.7% above baseline, respectively, and an overall decrease in SVR of 9.7+2.4% below baseline (all P<0.02). Serum relaxin and osmolality were 36+3 ng/ml and 287+1 mOsm/kg water, respectively. The latter significantly decreased compared to vehicle infusion.

Arterial Pressure Waveforms. Representative arterial waveforms from a single rat at baseline and after administration of rhRLX are depicted in FIG. 3A. They illustrate that the mouse pressure catheter (TA 11PA-C20) provides high fidelity recordings necessary for determining global AC. Ensemble average arterial pressure waveforms, derived using the methodology proposed by Burattini et al. (supra) are shown in FIG. 3B for the 3 groups of rats on day 10 of infusion. As discussed above, SV significantly increased and SVR significantly decreased following rhRLX administration (Tables 2 and 3). If these were the only alterations, one would expect to see a clear change in pressure waveform morphology: increased pulse pressure and hastened diastolic decay of arterial pressure. However, as illustrated in FIG. 3B, rhRLX administration did not significantly affect pressure waveform morphology, as indicated by unchanged pulse pressure and diastolic decay. This invariant pressure waveform morphology, in the presence of increased SV and decreased SVR, is consistent with a simultaneous increase in global AC.

In Vitro Studies

Arterial Passive Mechanics. These in vitro experiments were performed to examine the effects of rhRLX administration on passive (i.e., in the absence of active smooth muscle tone) mechanical properties of vascular wall. As mentioned before (Methods section), primary measurements consisted of vessel inner and outer diameters at various levels of intraluminal pressure. Circumferential wall stress ($\sigma$) and midwall radius ($R_m$) were calculated from these primary measurements and $\sigma$-$R_m$ relationship was used to quantify vessel wall elastic behavior (e.g., incremental elastic modulus, $E_{inc}$). $\sigma$-$R_m$ (FIG. 4A) and $E_{inc}$-$R_m$ (FIG. 4B) relationships for small renal arteries were significantly different between the two groups (P<0.001 by analysis of excess variance) such that $\sigma$ and $E_{inc}$ were smaller for a given $R_m$ in the relaxin-treated group. In contrast, the unstressed $R_m$, $R_{mo}$ (i.e., $R_m$ at $\sigma$=0), was not different between the two groups (relaxin-treated: 105±5 µm; vehicle-treated: 98±6 µm). Thus, the $R_m$ axis can be considered as circumferential wall strain. These data indicate that relaxin treatment significantly reduced vessel wall stiffness ($E_{inc}$) at matched $R_m$ (strain) values. This reduced passive wall stiffness contributes to the increased global AC seen in conscious animals with relaxin treatment (vide supra).

Example 2

Effects of Relaxin on Systemic Arterial Hemodynamics and Mechanical Properties in Conscious Rats: Sex Dependency and Dose Response Methods Animals Long-Evans male and female rats of 12-14 weeks were purchased from Harlan Sprague-Dawley (Frederick, Md. USA). They were provided PROLAB RMH 2000 diet containing 0.48% sodium (PME Feeds Inc., St. Louis, Mo. USA) and water ad libitum. The rats were maintained on a 12:12-h light-dark cycle. This investigation conforms with the Guide for the Care and Use of Laboratory Animals published by the US National Institute of Health (NIH Publication No. 85-23, revised 1996).

Administration of Recombinant Human Relaxin (rhRLX)

The rhRLX (BAS, Palo Alto, Calif. USA) was provided as a 5.0 mg/ml solution in a buffer (20 mM sodium acetate, pH 5.0). It was diluted as necessary in the same buffer. For the low dose infusion protocol, two model 2002 osmotic minipumps (Durect Corporation, Cupertino, Calif. USA) were used to deliver the rhRLX for 10 days at the dose of 4 µg/h. This dose was designed to yield concentrations of circulating relaxin similar to those measured during early to midgestation in rats, i.e., 10-20 ng/ml (Sherwood O D, Endocrinol Rev 25(2): 205-234, 2004). For the high dose infusion protocol, one model 2ML2 osmotic minipump was used to deliver rhRLX at 50 µg/h for 6 days, which was expected to produce serum concentrations comparable to those recorded during late gestation (Sherwood O D, Endocrinol Rev 25(2): 205-234, 2004) when further increases in CO and decreases in SVR are observed in this species (Gilson et al., Am J Physiol 32: H1911-H1918, 1992; Slangen et al., Am J Physiol 270: Hi779-1784, 1996). Finally, in a third protocol, rhRLX was administered by i.v. bolus over 3 min (13.4 µg/ml) followed by a continuous i.v. infusion for 4 hours.

Surgical Preparation

As in Example 1, rats were anesthetized with 60 mg/kg ketamine i.m. and 21 mg/kg pentobarbital i.p. They were then instrumented, using sterile technique, as follows: (i) a tygon catheter implanted in the right jugular vein with the tip lying at the junction of the anterior vena cava and right atrium, (ii) a thermodilution microprobe (36 cm long, F#1.5; Columbus Instruments, Columbus, Ohio USA) implanted in the abdominal aorta via the left femoral artery with the tip lying 1.0 cm below the left renal artery, and (iii) a mouse pressure catheter (TA11PA-C20, F#1.2; Data Science International, St. Paul, Minn. USA) implanted in the right carotid artery with the tip lying at the junction of the right carotid artery and aortic arch. For the acute administration of rh PLX, another tygon catheter was implanted in the inferior vena cava via the left femoral vein such that the tip lay 1.0cm below the right renal artery.

After instilling 0.05 ml of a heparin solution into the jugular catheter and plugging it with a straight pin, rats were given ampicillin by drinking water for 2 days (100 mg/50 ml with 2 tablespoons of dextrose). Terbutrol was given s.c. for postoperative analgesia.

For chronic administration of low dose recombinant human relaxin (4.0 µg/h rhRLX) in the male rats for 10 days, two Alzet model 2002 osmotic minipumps (Durect Corporation, Curpertino, Calif. USA) were inserted subcutaneously in the back of the animal under isoflurane anesthesia. For chronic high dose administration in the female rats for 6 days (80 µg/h), one Alzet model 2ML2 osmotic minipump was implanted. High dose rhRLX was also administered to another group of female rats acutely by intravenous bolus over 3 min (13.4 µg/ml) followed by a continuous infusion for 4h.

After completion of the measurement for the last time point, rats were anesthetized with 60 mg/kg pentobarbital i.v. Blood was obtained from the abdominal aorta for measurements of plasma rhRLX levels. The position of the jugular catheter relative to the right atrium, the placement of the pressure catheter relative to the aortic arch, and the position of the thermocouple relative to the left renal artery were recorded.

Hemodynamics and Systemic Arterial Mechanical Properties

The low and high dose rhRLXprotocols entailed 7 male and 9 female rats, respectively. After two baseline measurements of systemic hemodynamics on days 5 and 7 after surgery, either low or high dose rhRLX was administered by osmotic minipump. Systemic hemodynamics were again assessed on days 3, 6, 8 and 10 after initiation of relaxin infusion for the low dose male rats and days 3 and 6 for the high dose female rats. Each measurement consisted of 4 to 8 recordings of cardiac output and blood pressure waveforms obtained when the rat was either sleeping or resting. Seven to 10 minutes were allowed between recordings. These measurements were obtained between 9 AM and 3 PM.

For acute administration of high dose rhRLX, 5 female rats were used. Baseline measurements of systemic hemodynamics were obtained followed by intravenous infusion of high dose rhRLX for 4 hours. Systemic hemodynamics were assessed continuously during the 4 hour infusion.

We used the thermodilution technique (Osbom et al., *Am J Physiol* 251: H1365-H1372, 1986) to measure cardiac output. Instantaneous aortic pressure waveforms were recorded using a blood pressure telemetry system (Data Sciences International, St. Paul, Minn. USA) (Mills et al., *J Appl Physiol* 88: 1537-1544, 2000). The aortic pressure recorded by the pressure catheter implanted in the aortic arch was transmitted to an external receiver. Steady-state aortic pressure was digitized online using a PC-based data acquisition system with 16 bit resolution and 2000 Hz sampling rate and stored as text files for off-line analysis. Each measurement consisted of a 30 second sampling duration.

Analysis of the acquired data and calculation of global AC was performed using a custom computer program developed using Matlab software (MathWorks Inc., Natick, Mass. USA). Briefly, individual beats were selected (3-15 cycles) from the 10 seconds of the aortic pressure recording, immediately preceding the measurement of cardiac output. The ensemble was averaged as described by Burattini et al. (2) to yield a single representative beat for each trial. The mean arterial pressure (MAP), peak systolic pressure ($P_s$), and end diastolic pressure ($P_d$) were calculated from this averaged beat. Pulse pressure (PP) was calculated as $P_s$-$P_d$. Systemic vascular resistance (SVR) was calculated by dividing the MAP by CO.

Two measures of global arterial compliance were calculated. The first ($AC_{area}$) was calculated from the diastolic decay of the aortic pressure waveform [P(t)] using the area method (18):

$$AC_{area}=A_d/[SVR(P_1-P_2)]$$

where $P_1$ and $P_2$ are the pressures at the beginning and end of the diastolic decay curve, respectively, and $A_d$ is the area under the P(t) waveform over this region. The second measure of global arterial compliance was calculated as the stroke volume-to-pulse pressure ratio, SV/PP (Chemla et al., *Am J Physiol* 274: H500-H505, 1998). Stroke volume was defined as CO/HR.

Serum Measurements

Serum osmolality was measured using a freezing-point depression instrumentation osmometer (Model 3 MO; Advanced Instruments, Needham Heights, Mass. USA). The levels of rhRLX in serum were measured by a quantitative sandwich immunoassay as previously described (Jeyabalan et al., *Circ Res* 93: 1249-1257, 2003).

Statistical Analysis

Data are presented as means±SEM. Data from a previous study (Conrad et al., *Endocrinology* 145(7): 3289-3296, 2004; Example 1) wherein low and medium doses of rhRLX were administered to female rats are included for comparison. Two-factor repeated measures ANOVA (Zar J H, *Biostatistical Analysis*. Englewood Cliffs: Prentice Hall, 1984) was used to compare mean values between low dose male and female rats at various time points. The same analysis was performed to compare mean values among low, medium, and high doses of rhRLX in female rats at various time points. One-factor repeated measures ANOVA (Conrad et al., *Endocrinology* 145(7): 3289-3296, 2004) was used to compare mean values at various time points following initiation of high dose rhRLX acute infusion to baseline values. If significant main effects or interactions were observed, pairwise comparisons between groups were performed using Fisher's LSD test. The student's paired 't' test was used to compare the composite mean values (defined later) during chronic infusion of rhRLX with baseline. P<0.05 was taken to be significant. Finally, linear regression was used to analyze the relationships between the magnitudes of the change in each arterial property of individual rats in response to relaxin infusion and the baseline values of that property. Group differences in the linear regression parameters were examined using ANCOVA, implemented as multiple linear regression with dummy variables (Gujarati D, *Am Statistician* 24: 18-22, 1970).

Results

Figure 5:
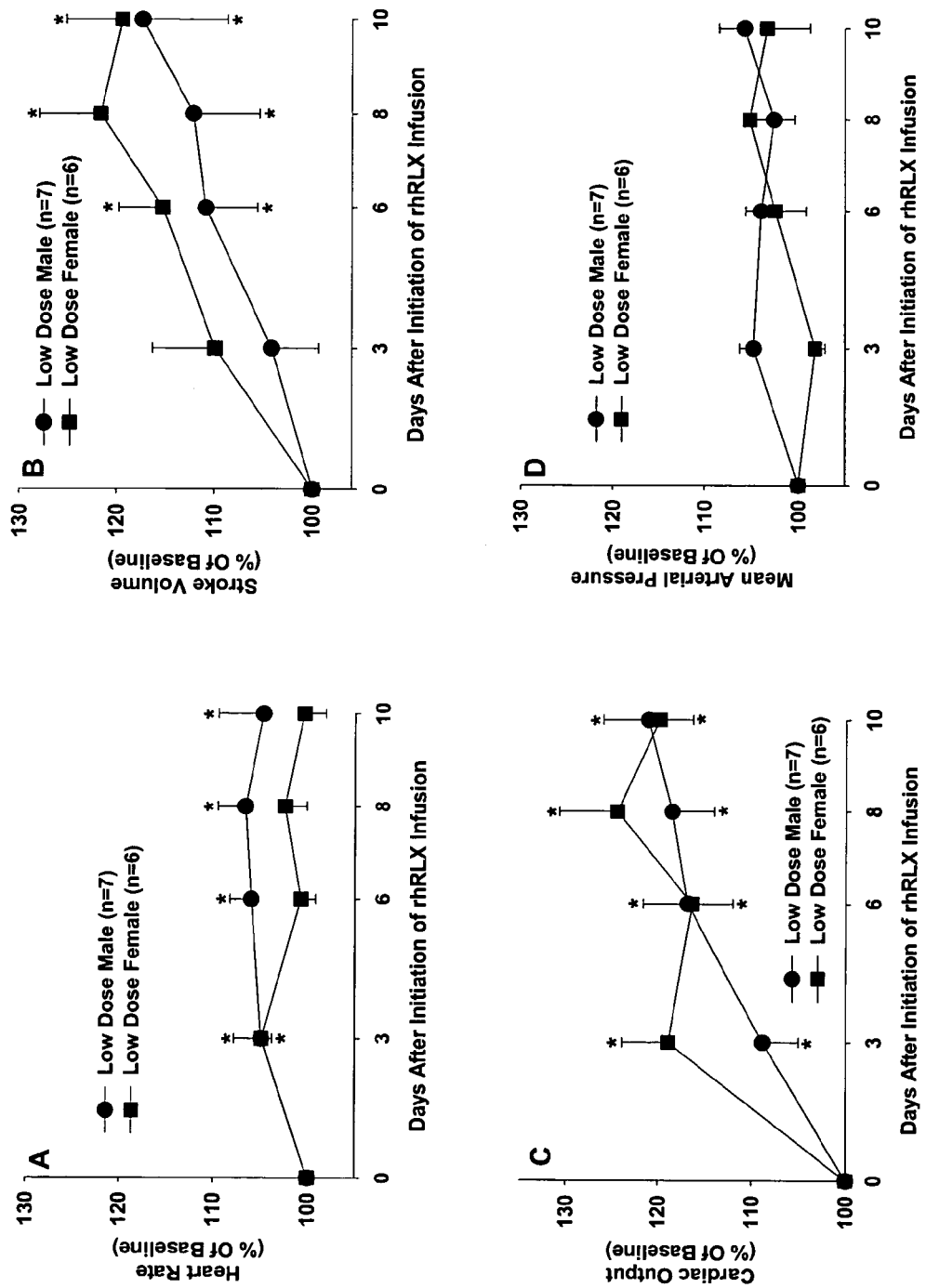
FIG. 5 shows temporal changes in systemic hemodynamics in response to low dose (4 µg/h) recombinant human relaxin administration in male and female rats. Heart rate (A), stroke volume (B), cardiac output (C), and mean arterial pressure (D) data are presented as percentages of baseline. * $P<0.05$ vs. baseline (post-hoc Fisher's LSD). Significant increments in SV are shown only for days 6, 8 and 10.

Male Rats Administered Low Dose rhRLX(4 µg/h). The temporal patterns of several systemic hemodynamic variables, expressed as a percentage of baseline values, are illustrated in FIG. 5 and absolute values of these variables are presented in Table 4. For the purpose of comparison, the data from our previous study (Conrad et al., *Endocrinology* 145 (7): 3289-3296, 2004) examining the effects of rhRLX infusion at 4 µg/h in female rats are also presented in FIG. 5. Low dose rhRLX significantly increased CO relative to baseline in male rats. There was a slight (~6%), but statistically significant, rise in HR in the relaxin-treated male rats (FIG. 5A). However, there was a greater rise in SV (FIG. 5B) indicating that the elevation in CO resulted primarily from an increase in SV, and to a lesser degree from a rise in HR. Mean arterial pressure was not significantly changed during rhRLX infusion (FIG. 5D). At the final time point (i.e., day 10 after the onset of rhRLX infusion), there was no statistically significant difference between the effects of rhRLX administration on systemic hemodynamics in the male and female rats.

Figure 6:
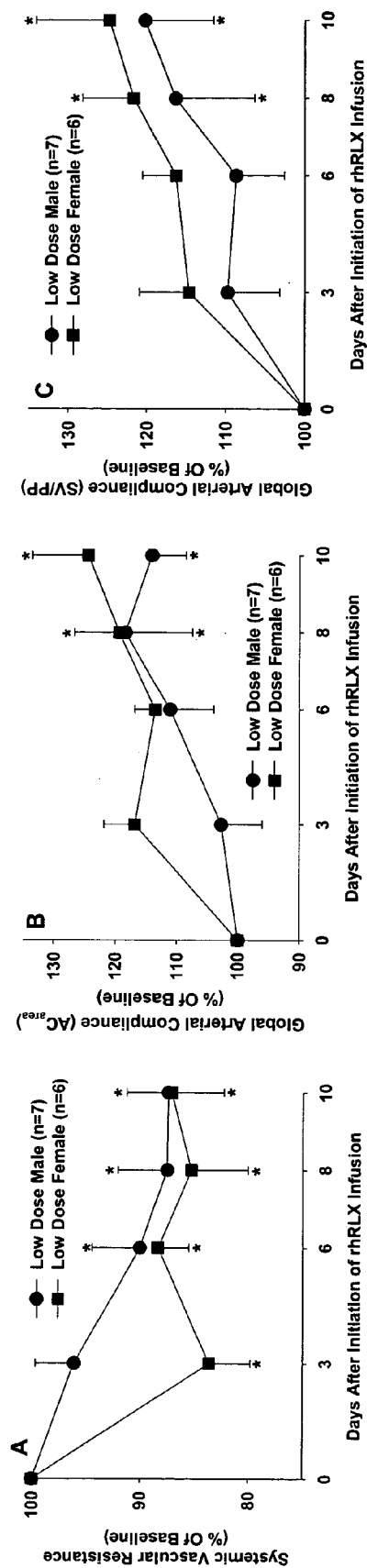
FIG. 6 depicts temporal changes in systemic arterial properties in response to low dose (4 μg/h) recombinant human relaxin administration in male and female rats. Systemic vascular resistance (A) and two measures of global arterial compliance, $AC_{area}$ (B) and SV/PP (C), data are presented as percentages of baseline. *$P<0.05$ vs. baseline (post-hoc Fisher's LSD). Significant increments in $AC_{area}$ and SV/PP are shown only for days 8 and 10.
Figure 7:
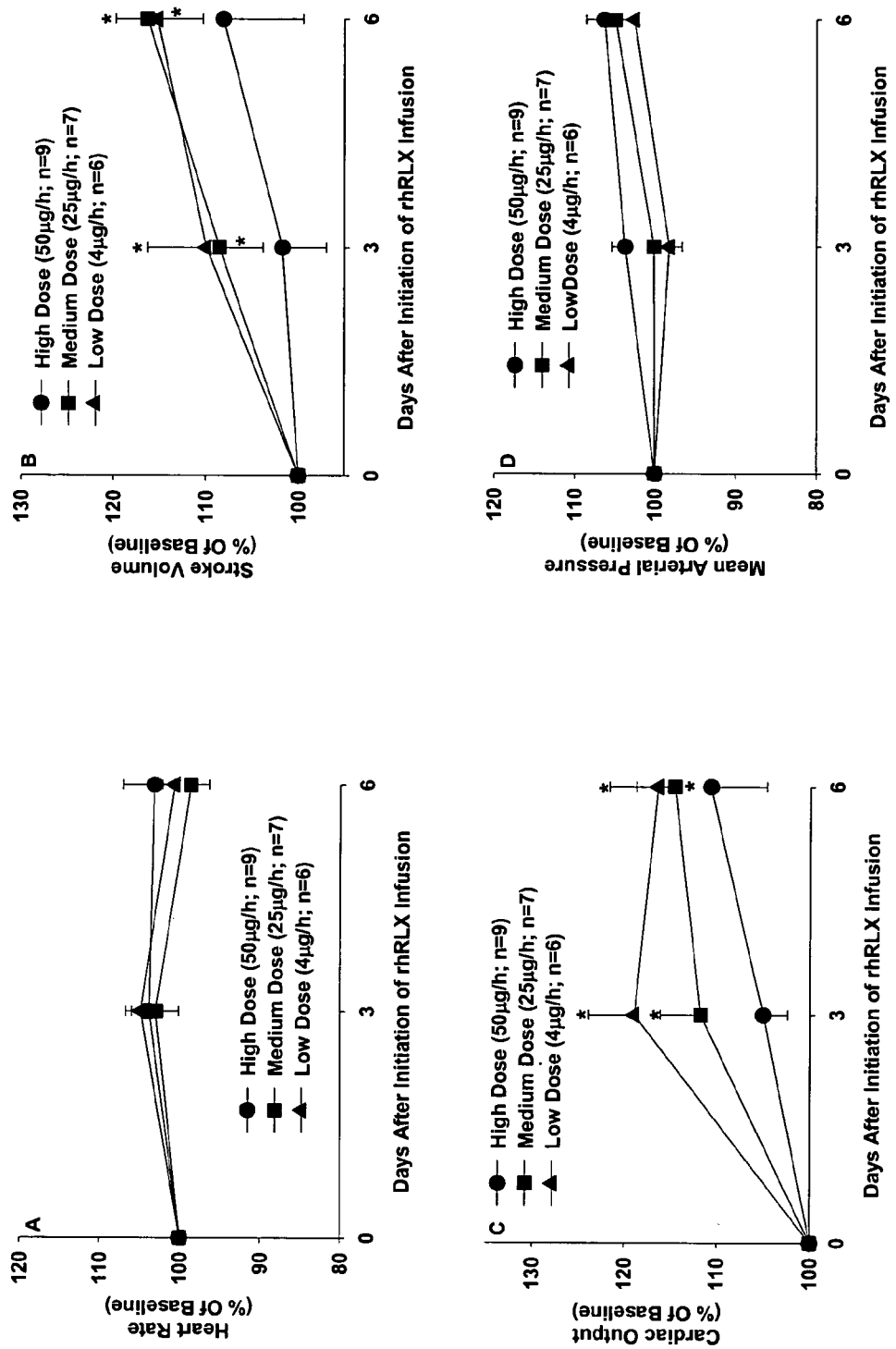
FIG. 7 depicts temporal changes in systemic hemodynamics in response to three doses of recombinant human relaxin administration in female rats: low (4 μg/h), medium (25 μg/h), and high (50 μg/h). Heart rate (A), stroke volume (B), cardiac output (C), and mean arterial pressure (D) data are presented as percentages of baseline. *$P<0.05$ vs. baseline (post-hoc Fisher's LSD).
Figure 8:
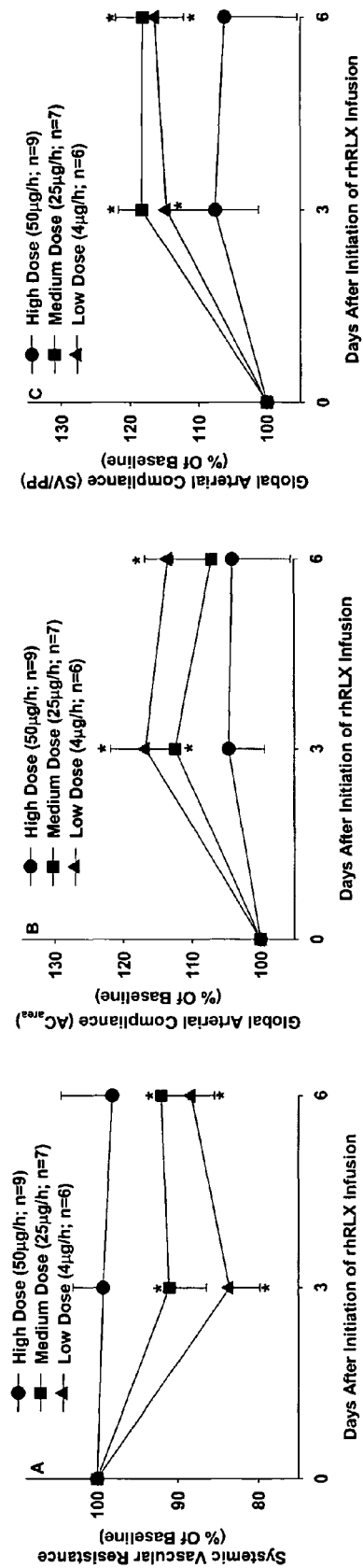
FIG. 8 depicts temporal changes in systemic hemodynamics in response to three doses of recombinant human relaxin administration in female rats: low (4 μg/h), medium (25 μg/h), and high (50 μg/h). Systemic vascular resistance (A) and two measures of global arterial compliance, $AC_{area}$ (B) and SV/PP (C), data are presented as percentages of baseline. *$P<0.05$ vs. baseline (post-hoc Fisher's LSD).

The temporal effects of rhRLX infusion on systemic arterial properties in male rats, expressed as a percentage of baseline values, are depicted in FIG. 6. Once again, absolute values for these variables are presented in Table 4 and data from female rats are also shown in FIG. 6 for comparison. Systemic vascular resistance fell significantly relative to baseline (FIG. 6A), while both measures of arterial compliance ($AC_{area}$ and SV/PP) were significantly increased (FIGS. 2B and 2C). At the final time point (i.e., day 10 after the onset of rhRLX infusion), the changes in arterial properties were not statistically different between male and female rats.

TABLE 4

Male Rats Administered Low Dose rhRLX (4 μg/h)

| Days After Minipump | $\Delta_T$ (° C.) | CO* (mL/min) | HR* (bpm) | SV* (mL) | $AC_{area}$* (μl/mmHg) | SVR* (mmHg.s/mL) | MAP (mmHg) |
|---|---|---|---|---|---|---|---|
| Baseline | 0.32 ± 0.03 | 148 ± 9 | 416 ± 12 | 0.36 ± 0.03 | 7.5 ± 0.6 | 49 ± 3 | 115.8 ± 2.4 |
| 3 | 0.31 ± 0.01 | 160 ± 6 | 440 ± 8 | 0.36 ± 0.01 | 7.6 ± 0.5 | 46 ± 1 | 121.3 ± 3.6 |
| 6 | 0.29 ± 0.02 | 169 ± 4 | 441 ± 6 | 0.38 ± 0.01 | 7.9 ± 0.3 | 43 ± 1 | 119.9 ± 1.7 |
| 8 | 0.27 ± 0.02 | 178 ± 6 | 445 ± 4 | 0.40 ± 0.01 | 8.7 ± 0.4 | 41 ± 1 | 118.8 ± 2.0 |
| 10 | 0.28 ± 0.02 | 183 ± 11 | 442 ± 5 | 0.41 ± 0.02 | 8.8 ± 0.5 | 41 ± 2 | 121.6 ± 2.6 |

Mean±SEM. N=7 rats. $\Delta_T$, change in blood temperature after injection of Ringer's solution into the right heart; CO, cardiac output; HR, heart rate; SV, stroke volume; $AC_{area}$, global arterial compliance calculated using area method; SVR, systemic vascular resistance; MAP, mean arterial pressure. *P<0.05 by single factor repeated measures ANOVA.

We calculated a composite mean change from baseline for each variable by averaging values at all successive time points during the infusion of rhRLX that were characterized by a significant change from baseline and were not significantly different from each other (i.e., the plateau phase). This yielded overall increases in CO and global AC of 20.5±4.2% and 19.4±6.9% from baseline, respectively, and an overall decrease in SVR of 12.7±3.9% from baseline (all P<0.05 vs. baseline). There was no statistical difference between these results in male rats and those reported for female rats (Example 1). Serum rhRLX was 17.7±1.1 ng/ml, a value similar to that previously observed in female rats administered the same rhRLX regimen, 14.0±2.0 ng/ml.

Figure 3:
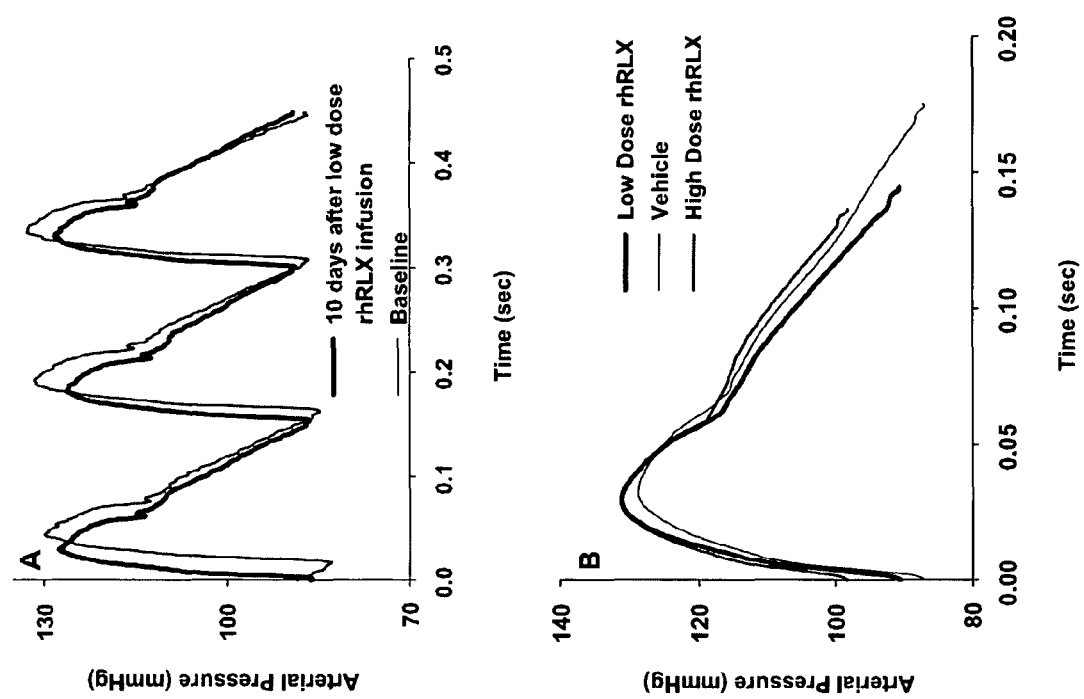
FIGS. 3A and 3B depict representative arterial pressure tracings from one rat (FIG. 3A); and ensemble average arterial pressure waveforms for the three groups (vehicle, low dose rhRLX, and high dose rhRLX) at day 10 after implantation of the osmotic minipump (FIG. 3B).
Figure 4:
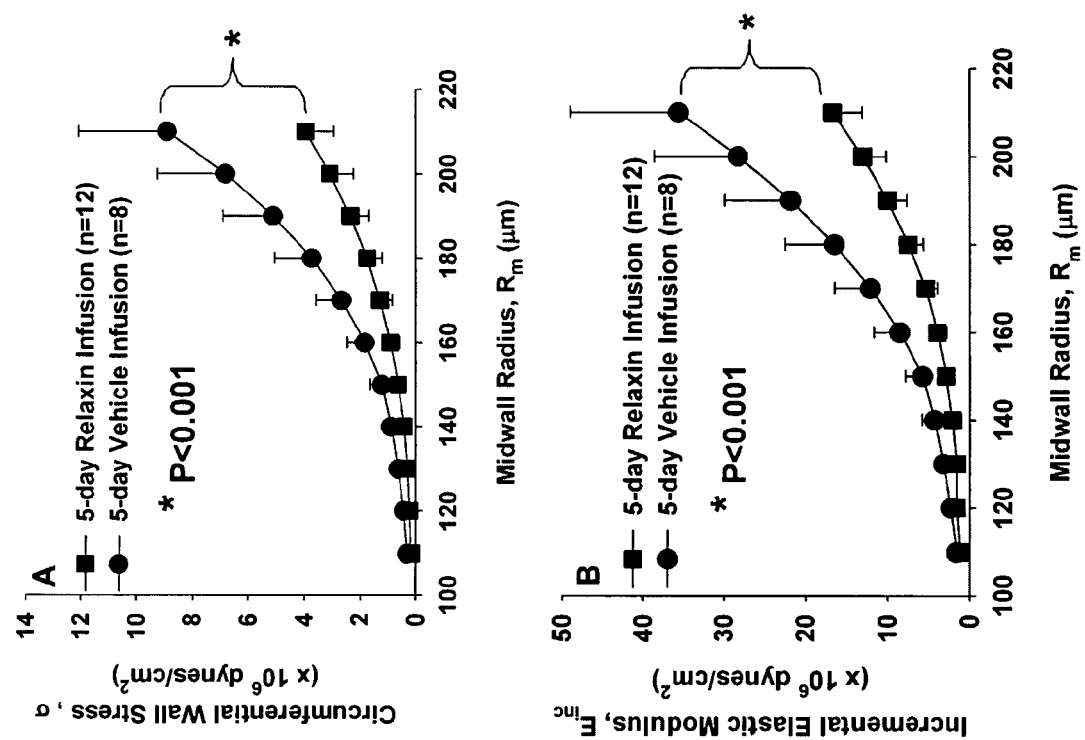
FIGS. 4A and 4B depict circumferential stress ($\sigma$)-midwall radius ($R_m$) (FIG. 4A); and incremental elastic modulus ($E_{inc}$)-$R_m$ (FIG. 4B) relationships for small renal arteries isolated from rats treated with rhRLX or vehicle for 5 days.

Female rats administered high dose rhRLX(50 μg/h). Absolute values of systemic hemodynamics and arterial properties are listed in Table 5 and their temporal patterns following the initiation of rhRLX infusion are depicted in FIGS. 3 and 4. For the purpose of comparison, data from Example 1 examining the effects of low (serum concentration=14±2 ng/ml) and medium (serum concentration=36±3 ng/ml) dose rhRLX infusion in female rats are also shown in FIGS. 3 and 4. Low and medium dose rhRLX infusion significantly increased CO, mainly by increasing SV. Both doses also significantly reduced SVR and increased AC (Conrad et al., *Endocrinology* 145(7): 3289-3296, 2004). These alterations were all observed by the earliest time point studied—3 days after the onset of rhRLX administration. Serum rhRLX concentration for the high dose infusion in the present study was 71.5±1.6 ng/ml. However, there was no change from baseline in any of the systemic hemodynamics or arterial properties (FIGS. 3 and 4). Thus, the effects of rhRLX on systemic hemodynamics and arterial properties are apparently biphasic.

Mean±SEM. N=8 rats. $\Delta_T$, change in blood temperature after injection of Ringer's solution into the right heart; CO, cardiac output; HR, heart rate; SV, stroke volume; $AC_{area}$, global arterial compliance calculated using area method; SVR, systemic vascular resistance; MAP, mean arterial pressure. *P<0.05 by single factor repeated measures ANOVA.

Figure 9:
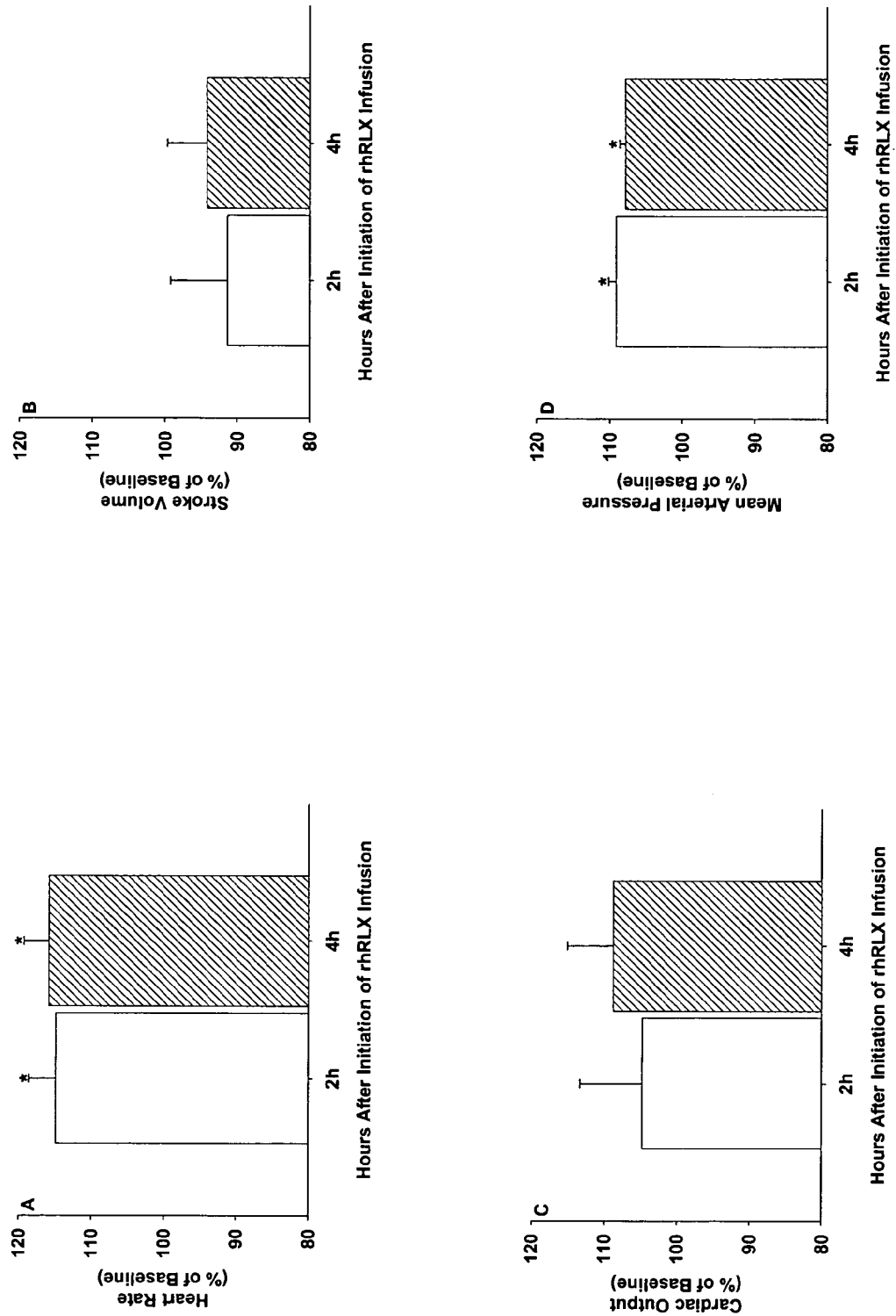
FIG. 9 depicts temporal changes in systemic hemodynamics in response to short-term high dose recombinant human relaxin administration in female rats. Heart rate (A), stroke volume (B), cardiac output (C), and mean arterial pressure (D) data are presented as percentages of baseline. *$P<0.05$ vs. baseline (post-hoc Fisher's LSD).
Figure 10:
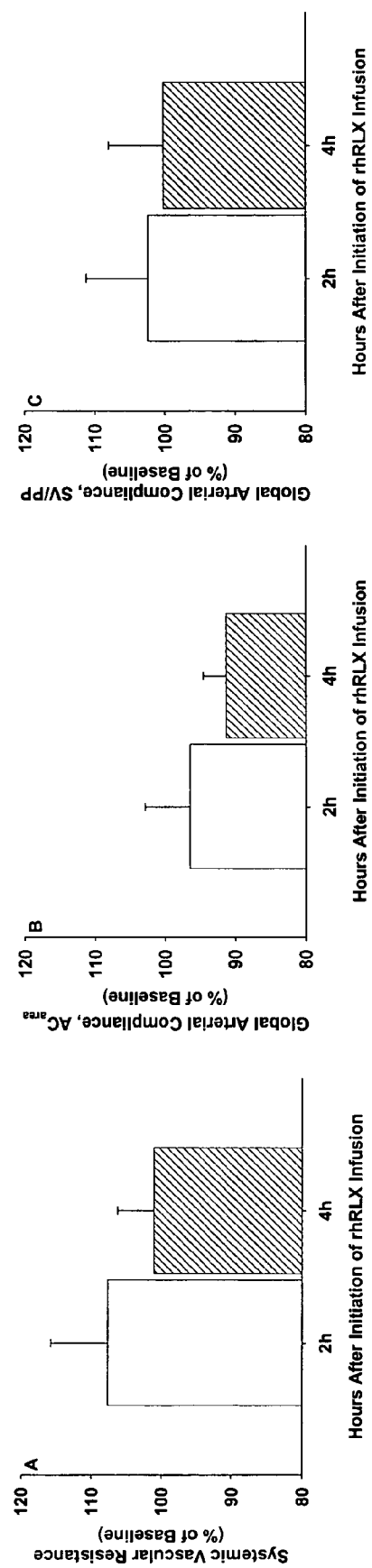
FIG. 10 depicts temporal changes in systemic arterial properties in response to short-term high dose recombinant human relaxin administration in female rats. Systemic vascular resistance (A) and two measures of global arterial compliance, $AC_{area}$ (B) and SV/PP (C), data are presented as percentages of baseline.
Figure 11:
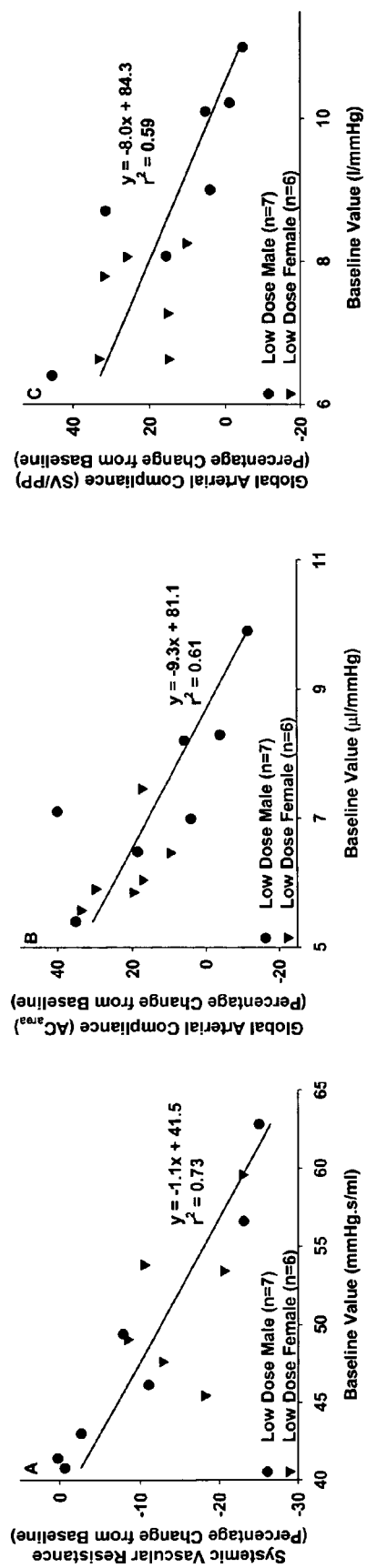
FIG. 11 depicts relationships between composite percentage changes from baseline and baseline values for systemic vascular resistance (A) and two measures of global arterial compliance, $AC_{area}$ (B) and SV/PP (C), in male and female rats administered low dose recombinant human relaxin (4 μg/h). These relationships were gender-independent. The solid line in each panel corresponds to the plot of the relationship obtained by linear regression (male and female rats combined).

To determine whether there would be significant alterations in systemic hemodynamics and arterial properties in response to high dose rhRLX treatment at a time point earlier than 3 days after the onset of rhRLX administration, an additional 5 female, conscious rats were treated with acute i.v. infusion of rhRLX over 4 hours. Serum rhRLX concentration was 64.1±1.0 ng/ml. The temporal effects of short-term, high dose rhRLX infusion on systemic hemodynamics and arterial properties in female rats, expressed as a percentage of baseline values, are depicted in FIGS. 5 and 6. Heart rate was significantly increased (~13%) at both the 2 and 4 hour time points (FIG. 9A). This increase in HR was offset by a decrease (although statistically insignificant) in SV (FIG. 9B), resulting in no significant change in CO (FIG. 9C). There was a small (~8%), but statistically significant, increase in MAP (FIG. 9D). There were no statistically significant changes from baseline in any of the systemic arterial properties (FIG. 9).

The above-described data suggests that the magnitude of the change in arterial properties of individual rats (male or female) in response to infusion of low dose rhRLX was dependent on the baseline value of that particular property. To validate this trend, the relationship between baseline values of SVR, $AC_{area}$ and SV/PP and their respective composite percentage changes from baseline during rhRLX infusion was analyzed. Linear regression analysis revealed that the effect of rhRLX infusion (i.e., the percent change from baseline) on SVR (FIG. 9A) and AC, as measured by both $AC_{area}$ (FIG. 9B) and SV/PP (FIG. 9C), were all highly dependent on their baseline values. Specifically, rats with low AC at baseline were characterized by a greater increase in AC in response to relaxin treatment. Similarly, rats that had high SVR at baseline responded to relaxin with a greater decrease in SVR.

TABLE 5

Female Rats Administered High Dose rhRLX (50 μg/h)

| Days after minipump | $\Delta_T$ (° C.) | CO (mL/min) | HR (bpm) | SV (mL) | $AC_{area}$ (μl/mmHg) | SVR (mmHg.s/mL) | MAP* (mmHg) |
|---|---|---|---|---|---|---|---|
| Baseline | 0.34 ± 0.02 | 134 ± 5 | 425 ± 14 | 0.32 ± 0.02 | 7.0 ± 0.4 | 53 ± 2 | 115.9 ± 2.7 |
| 3 | 0.32 ± 0.02 | 141 ± 6 | 438 ± 6 | 0.32 ± 0.01 | 7.2 ± 0.3 | 52 ± 2 | 120.2 ± 3.3 |
| 6 | 0.31 ± 0.01 | 146 ± 6 | 437 ± 8 | 0.33 ± 0.02 | 7.4 ± 0.4 | 51 ± 3 | 121.1 ± 2.8 |

Further analysis (ANCOVA) indicated that these linear relationships were not different between male and female rats.

The results above show that relaxin elicits similar effects on systemic hemodynamics and arterial properties in both male and female rats even though relaxin is traditionally considered to be a female hormone and is not believed to circulate in male rats (Sherwood O D, *Endocrinol Rev* 25(2): 205-234, 2004).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for increasing arterial compliance in a subject, said method comprising:
   measuring global arterial compliance in said subject;
   determining that said global arterial compliance is diminished in said subject relative to global arterial compliance in a healthy subject; and
   administering to said subject a pharmaceutical formulation comprising relaxin to increase arterial compliance in said subject.

2. The method of claim 1, wherein said global arterial compliance is measured from the diastolic decay of the aortic pressure waveform using the area method.

3. The method of claim 1, wherein said global arterial compliance is calculated as the stroke volume-to-pulse pressure ratio, and wherein said stroke volume is defined as the ratio of cardiac output to heart rate.

4. The method of any of claims 1-3, wherein said global arterial compliance in said subject is increased by at least 10% following administration of said pharmaceutical formulation to said subject.

5. The method of any of claims 1-3, wherein said global arterial compliance in said subject is increased by 15-20% following administration of said pharmaceutical formulation to said subject.

6. The method of any of claims 1-3, wherein said pharmaceutical formulation is administered to said subject at a predetermined rate so as to maintain a serum concentration of relaxin of from 0.5 to 80 ng/ml.

7. The method of any of claims 1-3, wherein said relaxin is recombinant human relaxin.

8. The method of claim 1, wherein said recombinant human relaxin is H2 relaxin.

9. The method of any of claims 1-3, wherein said pharmaceutical formulation is an injectable formulation.

10. The method of any of claims 1-3, wherein said pharmaceutical formulation is a sustained release formulation.

11. The method of any of claims 1-3, wherein said pharmaceutical formulation is delivered by continuous infusion.

12. The method of any of claims 1-3, wherein said subject is diagnosed with one or more ailments selected from the group consisting of: atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia.

13. The method of any of claims 1-3, wherein said subject is a perimenopausal woman, a menopausal woman, or a postmenopausal woman.

14. A method for increasing arterial compliance in a subject, said method comprising:
   measuring local arterial compliance in said subject;
   determining that said local arterial compliance is diminished in said subject relative to global arterial compliance in a healthy subject; and
   administering to said subject a pharmaceutical formulation comprising relaxin to increase arterial compliance in said subject.

15. The method of claim 14, wherein said local arterial compliance in said subject is increased by at least 10% following administration of said pharmaceutical formulation.

16. The method of claim 14, wherein said arterial compliance in said subject is increased by 15-20% following administration of said pharmaceutical formulation.

17. The method of claim 14, wherein said pharmaceutical formulation is administered to said subject at a predetermined rate so as to maintain a serum concentration of relaxin of from about 0.5 to 80 ng/ml.

18. The method of claim 14, wherein said relaxin is recombinant human relaxin.

19. The method of claim 18, wherein said recombinant human relaxin is H2 relaxin.

20. The method of claim 14, wherein said pharmaceutical formulation is an injectable formulation.

21. The method of claim 14, wherein said pharmaceutical formulation is a sustained release formulation.

22. The method of claim 14, wherein said pharmaceutical formulation is delivered by continuous infusion.

23. The method of claim 14, wherein said subject is diagnosed with one or more ailments selected from the group consisting of: atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia.

24. The method of claim 14, wherein said subject is a perimenopausal woman, a menopausal woman, or a postmenopausal woman.

25. A method for increasing arterial compliance in a subject, said method comprising:
   measuring regional arterial compliance in said subject;
   determining that regional arterial compliance in said subject is diminished in said subject relative to global arterial compliance in a healthy subject; and
   administering to said subject a pharmaceutical formulation comprising relaxin to increase arterial compliance in said subject.

26. The method of claim 25, wherein said regional arterial compliance is measured using pulse wave velocity.

27. The method of claim 25, wherein said regional arterial compliance in said subject is increased by at least 10% following administration of said formulation to said subject.

28. The method of claim 25, wherein said regional arterial compliance in said subject is increased by 15-20% following administration of said pharmaceutical formulation to said subject.

29. The method of claim 25, wherein said pharmaceutical formulation is administered to said subject at a predetermined rate so as to maintain a serum concentration of relaxin of from about 0.5 to 80 ng/ml.

30. The method of claim 25, wherein said relaxin is recombinant human relaxin.

31. The method of claim 30, wherein said recombinant human relaxin is H2 relaxin.

32. The method of claim 25, wherein said pharmaceutical formulation is an injectable formulation.

33. The method of claim 25, wherein said pharmaceutical formulation is a sustained release formulation.

34. The method of claim 25, wherein said pharmaceutical formulation is delivered by continuous infusion.

35. The method of claim 25, wherein said subject is diagnosed with one or more ailments selected from the group consisting of: atherosclerosis, Type 1 diabetes, Type 2 diabetes, coronary artery disease, scleroderma, stroke, diastolic dysfunction, familial hypercholesterolemia, isolated systolic hypertension, primary hypertension, secondary hypertension, left ventricular hypertrophy, arterial stiffness associated with long-term tobacco smoking, arterial stiffness associated with obesity, arterial stiffness associated with age, systemic lupus erythematosus, preeclampsia, and hypercholesterolemia.

36. The method of claim 25, wherein said subject is a perimenopausal woman, a menopausal woman, or a postmenopausal woman.

37. The method of any one of claims 1-3, wherein said subject is diagnosed with one or more ailments selected from the group consisting of: atherosclerosis, coronary artery disease, scleroderma, stroke, diastolic dysfunction, left ventricular hypertrophy, arterial stiffness associated with long-term tobacco smoking, arterial stiffness associated with obesity, hypercholesterolemia, Type 1 diabetes, Type 2 diabetes, and systemic lupus erythematosus.

38. The method of claim 14, wherein said subject is diagnosed with one or more ailments selected from the group consisting of: atherosclerosis, coronary artery disease, scleroderma, stroke, diastolic dysfunction, left ventricular hypertrophy, arterial stiffness associated with long-term tobacco smoking, arterial stiffness associated with obesity, hypercholesterolemia, Type 1 diabetes, Type 2 diabetes, and systemic lupus erythematosus.

39. The method of claim 25, wherein said subject is diagnosed with one or more ailments selected from the group consisting of: atherosclerosis, coronary artery disease, scleroderma, stroke, diastolic dysfunction, left ventricular hypertrophy, arterial stiffness associated with long-term tobacco smoking, arterial stiffness associated with obesity, hypercholesterolemia, Type 1 diabetes, Type 2 diabetes, and systemic lupus erythematosus.

* * * * *

UNITED STATES PATENT AND TRADEMARK OFFICE
CERTIFICATE OF CORRECTION

PATENT NO.       : 7,878,978 B2
APPLICATION NO.  : 11/084670
DATED            : February 1, 2011
INVENTOR(S)      : Kirk P Conrad et al.

It is certified that error appears in the above-identified patent and that said Letters Patent is hereby corrected as shown below:

Column 1, line 15 of the specification replace "The U.S. government may have certain rights in this invention, pursuant to Grant No. RO 1 HL67937 awarded by the National Institutes of Health" with "This invention was made with government support under Grant No. RO 1 HL67937 awarded by the National Institutes of Health. The government has certain rights in the invention."

Signed and Sealed this
Twenty-seventh Day of November, 2012

David J. Kappos
*Director of the United States Patent and Trademark Office*